United States Patent [19]

Ginsberg

[11] Patent Number: 5,196,309

[45] Date of Patent: Mar. 23, 1993

[54] CHARACTERIZATION OF PLATELET AGGREGATION DISORDERS

[75] Inventor: Mark H. Ginsberg, San Diego, Calif.

[73] Assignee: The Scripps Research Institute, La Jolla, Calif.

[21] Appl. No.: 614,723

[22] Filed: Nov. 15, 1990

[51] Int. Cl.$^5$ .................. G01N 33/567; G01N 33/577
[52] U.S. Cl. .................................. 435/7.21; 435/7.24; 436/503; 436/548
[58] Field of Search ........................ 435/7.21, 7.24; 436/503, 548, 811; 935/110

[56] References Cited

U.S. PATENT DOCUMENTS 4,783,330  11/1988  Furie et al. ................. 424/1.1
4,820,505   4/1989  Ginsberg et al. .............. 424/9

OTHER PUBLICATIONS

Abrams, et al., *Blood* 70: abst. no. 1196 (1987).
Shattil et al., *J. Biol. Chem.* 260: 11107 (1985).
Lam, et al., *J. Biol. Chem.* 262: 947–950 (1987).
Frelinger, et al., *J. Biol. Chem.* 265: 6346 (1990).
Shadle et al., *J. Cell Biol.* 99: 2056–60 (1984).
Zamarron et al., *Blood* 74: 208a (Suppl. 1) (1989).
D'Souza et al., *J. Biol. Chem.* 265: 3440 (1990).
A. L. Frelinger III, *Jour. Biol. Chem.*, 263, 12397–12402, 1988.

Primary Examiner—David Saunders
Attorney, Agent, or Firm—Douglas A. Bingham; Thomas Fitting; April C. Logan

[57] ABSTRACT

Methods are described for characterizing platelet aggregation defects. The defects are characterized as activation, ligand binding, or post-occupancy defects. In one embodiment of the invention a Cam variant of Glanzmann's thrombasthenia is characterized as having a ligand binding defect. In another embodiment, a patient with myelofibrosis is identified as having an activation defect. Rapid analysis are afforded using fluorescence-activated flow cytometry. Also, diagnostic kits are described which comprise antibodies suitable for characterizing the above defects.

13 Claims, 3 Drawing Sheets

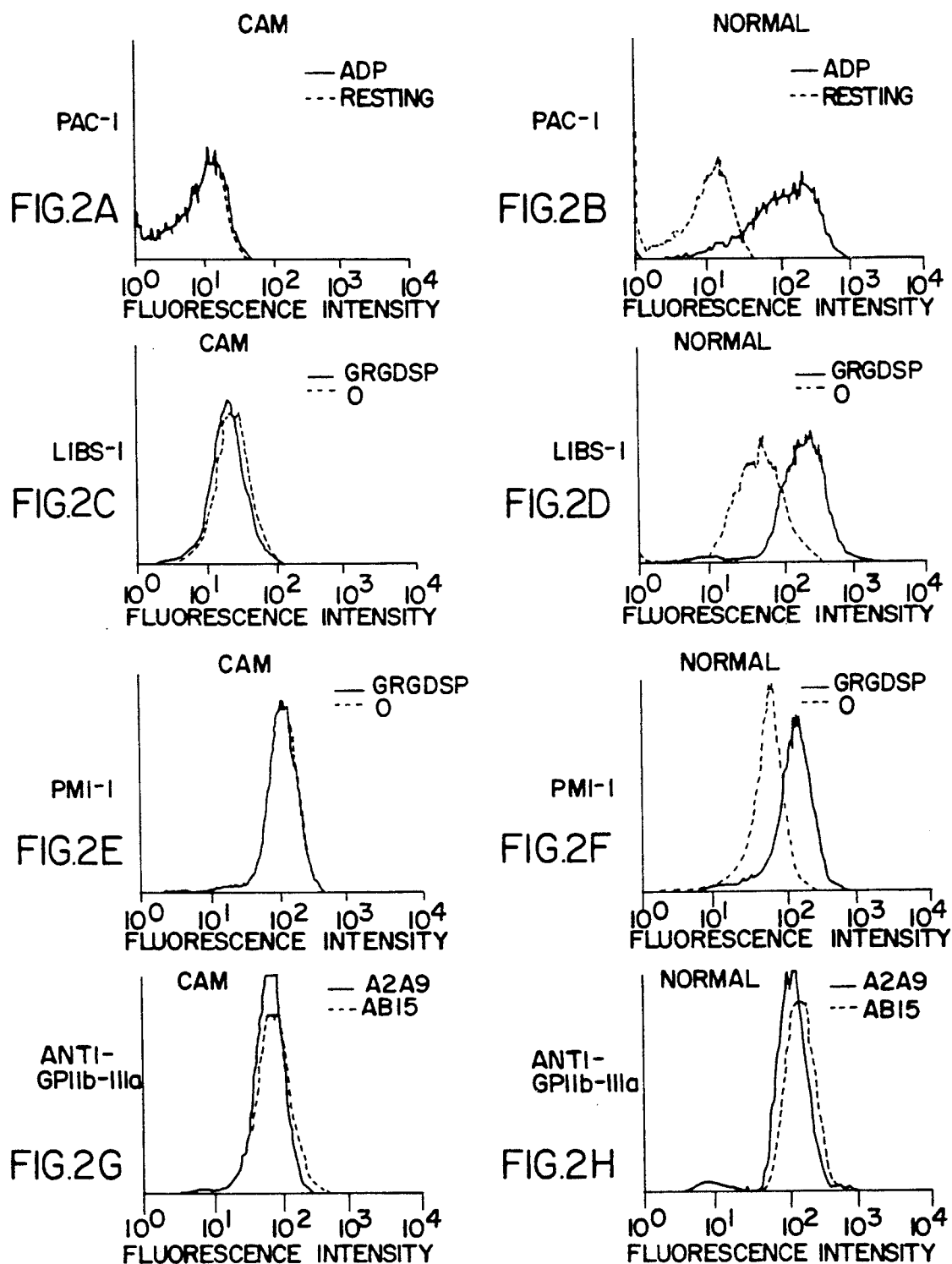

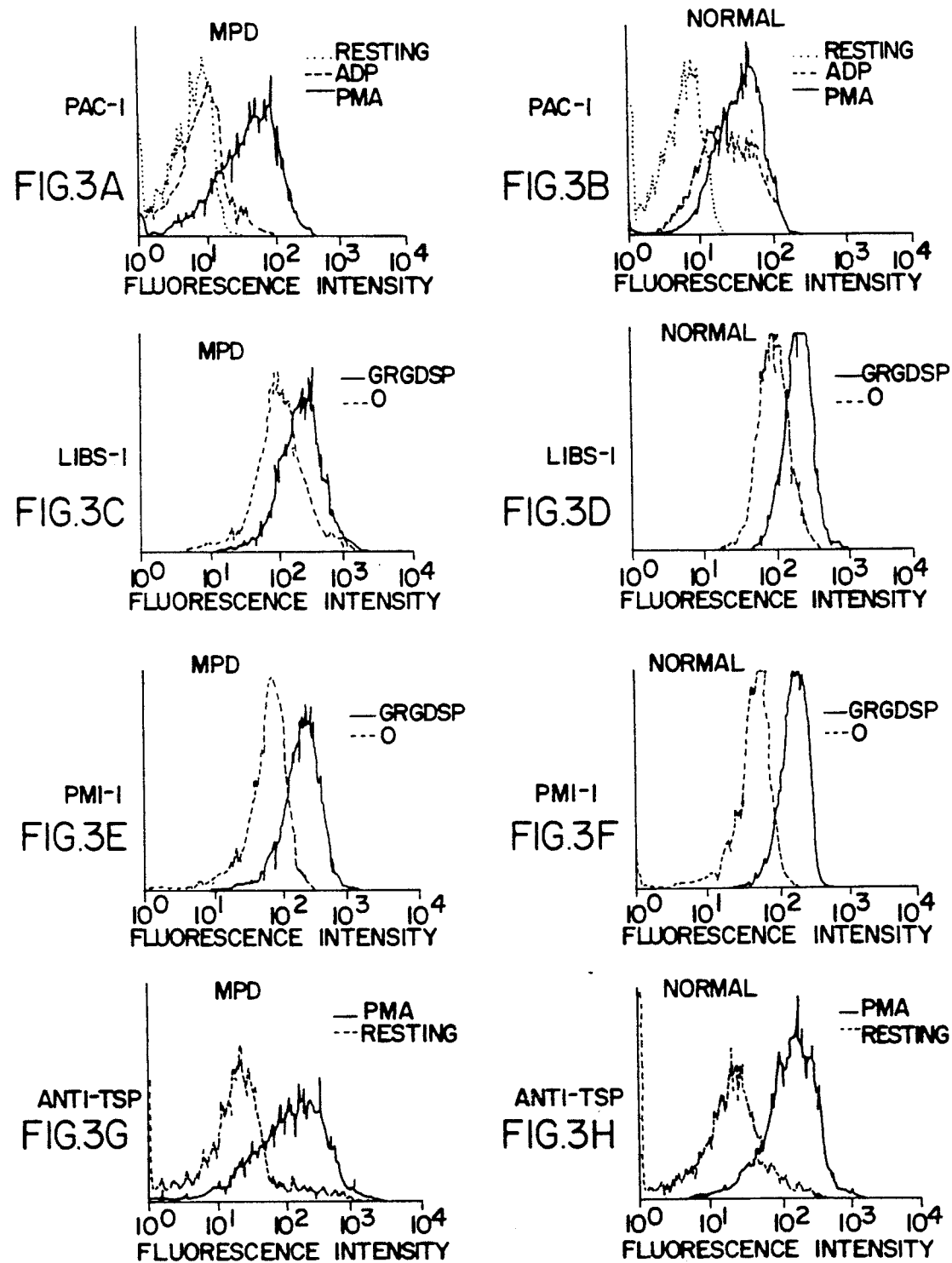

CHARACTERIZATION OF PLATELET AGGREGATION DISORDERS

This invention was made with government support under Government Contracts HL-31950 and HL-28235. The government has certain rights in the invention.

TECHNICAL FIELD

The present invention relates to the characterization of blood platelet disorders. The invention particularly relates to novel antibody systems and methods for characterizing platelet defects.

BACKGROUND

Primary platelet aggregation is essential for normal hemostasis and also plays a role in thrombosis. The results of studies on platelet aggregation over the past two decades indicate that normal platelet aggregation depends on the binding of fibrinogen to platelet glycoprotein GPIIb-IIIa. GPIIb-IIIa is a membrane glycoprotein of platelet cells which belongs to a class of extracellular receptors called Integrins. Patients having a deficiency in GPIIb-IIIa are observed to have prolonged bleeding times or bleeding diathesis due to platelet dysfunction.

The platelet aggregation process may be viewed as a series of necessary cellular events: 1) an agonist-induced activation of GPIIb-IIIa which results in exposure of the fibrinogen binding site; 2) binding of fibrinogen ligand to the exposed binding site of GPIIb-IIIa; and 3) post-occupancy events pursuant to ligand binding. All three steps are believed to be important to normal platelet aggregation. Thus, even when GPIIb-IIIa is present in the platelet membrane, dysfunction of any of the above steps may result in defective platelet aggregation.

Support for the above view of events leading to platelet aggregation is found in several recent studies. First, it is found that efficient binding of large GPIIb-IIIa ligands, such as fibrinogen or certain anti-GPIIb-IIIa antibodies, requires platelet activation by an agonist such as ADP or thrombin. See, e.g., Shattil et al., J. Biol. Chem., 260:11107 (1985). Additionally, it is found that small fibrinogen-mimetic ligands such as Arg-Gly-Asp (RGD)-containing peptides bind to GPIIb-IIIa independent of activation. See, e.g., Lam, Sc-t, et al., J. Biol. Chem., 262:947-950 (1987); Frelinger, A. L. III, et al., J. Biol. Chem., 263:12397-402 (1988). This has led to the hypothesis that the fibrinogen binding region of GPIIb-IIIa has only a limited accessibility to large ligands absent agonist-induced activation of the glycoprotein. Agonist-induced expression of the fibrinogen receptor is proposed to involve G protein-mediated activation of phospholipase C, followed by activation of protein kinase C. See Shattil, S. J., et al., J. Biol. Chem., 262:992-1000 (1987). The exact nature of the changes in GPIIb-IIIa that render it able to bind fibrinogen are presently undetermined.

Post-occupancy events involving the GPIIb-IIIa complex also appear to play a role in platelet aggregation. For example, when GPIIb-IIIa is bound to either fibrinogen or an RGD-containing peptide, it is observed that certain anti-GPIIb and anti-GPIIIa antibodies are capable of detecting the corresponding conformation change in the GPIIb-IIIa complex. This result suggests that conformational changes in the receptor/ligand complex occur subsequent to binding. How such conformational changes influence the extent of platelet aggregation is still unknown. See, e.g., Frelinger et al., supra; Frelinger et al., J. Biol. Chem., 265:6346 (1990). Moreover, conformational changes in the fibrinogen ligand are induced upon binding which may augment its adhesive function. See, e.g., Zamarron et al., Blood, 74:208a (Suppl. 1) (1989).

The most profound defects in platelet aggregation occur in patients afflicted with the hereditary disorder Glanzmann's thrombasthenia. The platelets of most homozygotes having the classic form of this disease possess less than 10% GPIIb-IIIa. In these individuals the observed defects in platelet aggregation can simply be attributed to the lack of functional GPIIb-IIIa.

However, other patients afflicted with Glanzmann's thrombasthenia display variant forms of the disease in which near normal levels of GPIIb-IIIa are present in the platelets. Accordingly, these latter individuals may have defects involving the activation, ligand binding, and/or post-occupancy functions of GPIIb-IIIa. Such defects are likely attributable to one or more primary defects in the amino acid sequence of GPIIb-IIIa.

Platelet aggregation defects are also observed in a number of clinical settings. For instance, myeloproliferative disorders, drug administration, uremia and post-cardiopulmonary bypass often involve acquired platelet aggregation defects. Such defects are likely to be attributable to one or more of the above described processes of activation, ligand binding, and post-occupancy defects.

Previous methods for diagnosing platelet aggregation dysfunction, e.g., platelet aggregeometry, have not afforded classification of the disorder in terms of the primary steps of activation, binding, and post-occupancy events. It is desirable to characterize the disorder in terms of one or more defects in such steps in order to more accurately diagnose a patient's condition. More accurate diagnoses are expected to lead to improved treatment programs for patients with platelet dysfunction. Improved definition of aggregation defects would also be of value in research settings, such as in characterizing the modes of action of proposed antiplatelet drugs.

BRIEF SUMMARY OF THE INVENTION

The present invention is for an improved method for characterizing platelet adhesion defects in a patient displaying platelet aggregation dysfunction. The method involves determining the presence of platelets which are activation competent in a first fluid sample from the patient. The presence of platelets having ligand occupancy competence is also determined in a second fluid sample from the patient. The results of the tests for activation competence and ligand occupancy competence are recorded and compared with predetermined criteria for characterizing platelet adhesion defects so that a deficiency of activation competent platelets in the first sample indicates an activation defect. A deficiency of ligand occupancy competent platelets in the second sample indicates a ligand binding defect. Sufficient amounts of activation competent and ligand-binding competent platelets indicate a post-occupancy defect whenever the patient does not exhibit normal platelet aggregation behavior.

The determination of activation competence preferably involves admixing the first platelet-containing sample with a predetermined amount of a platelet agonist which activates the platelets for binding. An activation specific ligand (ASL) is also admixed which preferentially binds with activated normal platelets relative to resting normal platelets. The ASL may also show somewhat increased binding to defective platelets subjected to activation conditions; however, the ASL will show greater binding affinity for activated normal platelets than for activated defective platelets. After maintaining the reaction mixture under predetermined conditions for a time sufficient for activated normal platelets to bind to the ASL, the amount of ASL-platelet reaction product formed in the sample is determined. In still further preferred embodiments of the invention, the activation specific ligand will be a monoclonal antibody such as PAC-1 (Shattil et al., *J. Biol. Chem.*, 260:11107 (1985)) and functional equivalents thereof, or fibrinogen.

Preferably, the analysis for ligand binding competence in the patient's platelets comprises admixing the second sample of bodily fluid with an activation independent ligand (AIL) sufficient to form a ligand-induced binding site (LIBS) on normal integrin-containing platelets. The sample is also mixed with an anti-LIBS antibody that immunoreacts with the ligand-induced binding site of the ligand-integrin complex. The ligand-occupancy competence of the examined platelets is determined by the amount of immunoreaction product formed. In a still further preferred embodiment of the invention, the AIL includes an RGD amino acid sequence and the anti-LIBS antibody probe is PMI-1, which is produced by the hybridoma having ATCC Accession Number HB9476.

The present invention also affords diagnostic kits that comprise an ASL, an AIL and an anti-LIBS antibody. In a preferred embodiment of the kits of the instant invention, the ASL will be PAC-1, its functional equivalents, or fibrinogen. The AIL preferably will be a polypeptide that includes an amino acid residue sequence such as RGD, LGGAKQAGDV, KYGRGDS, GRGDSP, and KQAGDV.

The novel methods and kits of the instant invention afford significant advantages over previous methods for characterizing platelet adhesion defects. The present invention can employ small sample sizes such as 0.5 mL as opposed to conventional aggregation methods that require 20 to 30 mLs. Also the present invention affords rapid analyses, taking less than thirty minutes in platelet rich plasma or whole blood. Most significantly, the instant invention affords improved definition of blood platelet aggregation defects in terms of the events of activation, ligand binding, and post-occupancy. Such characterization will find value in research and pharmaceutical industry settings. The instant methods may also lead to improved clinical treatments for patients having platelet dysfunction. Accordingly, the instant invention now affords characterization of platelet adhesion disorders such as the Cam variant of Glanzmann's thrombasthenia and myelofibrosis in terms of the aforementioned defects.

BRIEF DESCRIPTION OF THE DRAWINGS

FIGS. 2A through 2H show a flow cytometric analysis of the deficit in Cam variant of thrombasthenia. Shown are histograms with the log of fluorescence intensity on the abscissa and cell number on the ordinate. The reporting antibody is indicated in the left hand column. Cam platelets are shown in FIGS. 2A, 2C, 2E and 2G and the normal control in FIGS. 2B, 2D, 2F and 2H. Each column of figures contains a legend indicating the added agonist, peptide, or antibody. The ADP was added at a final concentration of 100 $\mu$mol/L; the GRGDSP was at a final concentration of 200 $\mu$mol/L. The bottom row depicts results with an anti-GPIIb-IIIa complex ($A_2A_9$) and an anti-GPIIIa (AB-15). Similar data were obtained with other antibodies to GPIIb-IIIa (7E3, 10E5, 4F10) and an antibody to GPIIb (Tab). The Cam variant data shown are representative of determinations on two affected male siblings with identical results.

FIGS. 3A through 3H show a flow cytometric analysis of aggregation dysfunction in a patient with myelofibrosis. Data obtained from platelets of a patient afflicted with myeloproliferative disease (MPD) are shown in FIGS. 3A, 3C, 3E and 3G, control platelets FIGS. 3B, 3D, 3F and 3H in. The disclosing antibody is indicated in the left hand column. In each column, the legend indicates the added agonist or peptide. Agonist and peptide concentrations were identical to those in FIGS. 2A-2H. Phorbol myristate acetate (PMA) was present in a final concentration of 50 nmol/L. Anti-TSP refers to the binding of a MoAb against thrombospondin.

DETAILED DESCRIPTION OF THE INVENTION

A. Definitions

Figure 1:
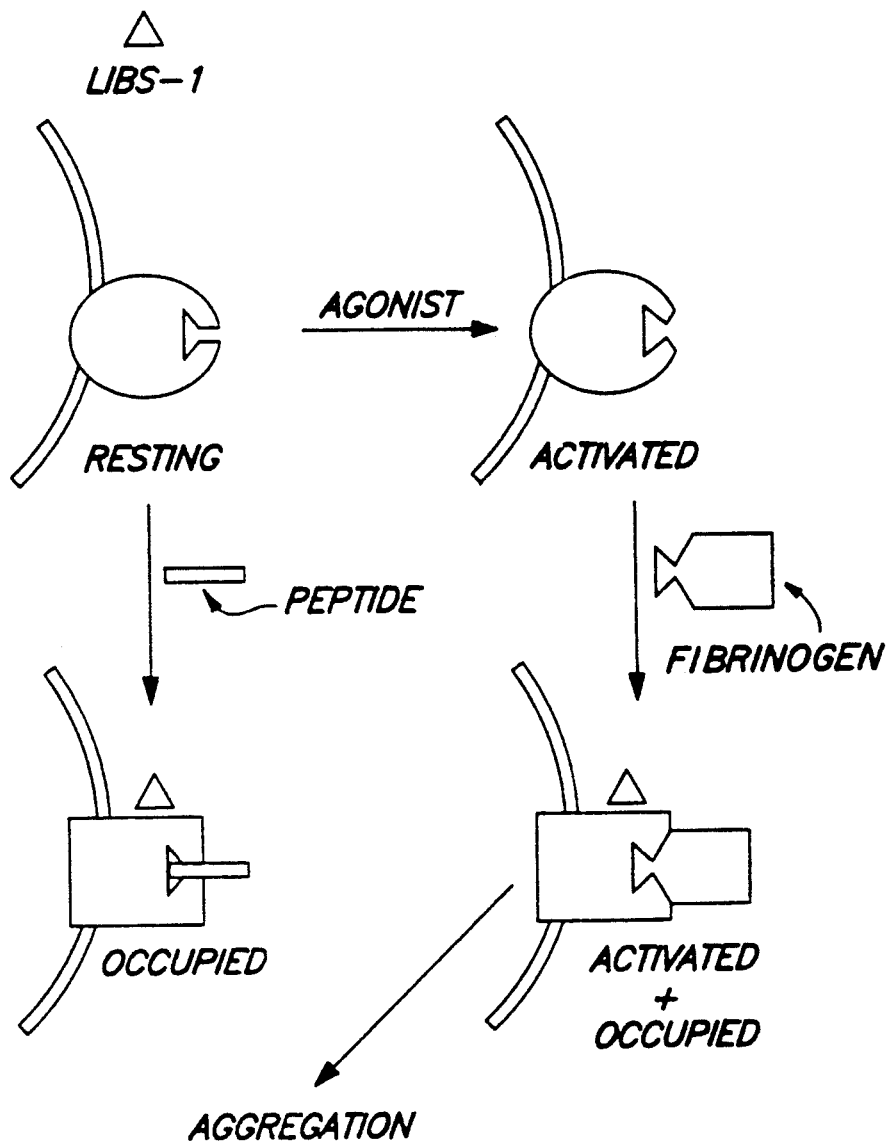
FIG. 1 shows a schematic representation of the proposed platelet aggregation mechanism. Depicted in the upper left hand corner is a GPIIb-IIIa-containing fibrinogen receptor on the surface of a resting platelet. This receptor has a ligand-binding pocket, but is not competent to bind macromolecular ligands such as fibrinogen or the PAC1 antibody. After activation with an agonist such as ADP, the ligand-binding pocket becomes accessible to macromolecular ligands such as fibrinogen and PAC1, as illustrated by the widening of the mouth of the pocket. After binding fibrinogen, the occupied receptor expresses occupancy-dependent epitopes such as LIBS 1. After this, through additional processes, the cells aggregate. The fibrinogen receptor can also be occupied by a small peptide ligand without prior activation, resulting in a conformation change with exposure of the LIBS 1 epitope (lower left corner;($\Delta$), anti-LIBS antibody).

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature (described in J. Biol. Chem., 243:3552–59 (1969) and adopted at 37 C.F.R. §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |

TABLE OF CORRESPONDENCE

| SYMBOL | | |
|---|---|---|
| 1-Letter | 3-Letter | AMINO ACID |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left to right orientation in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. §1.822(b)(4), and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxy-terminal group such as COOH.

Antibody: a polypeptide which chemically binds to a haptenic group, i.e., ligand. Antibodies, as used herein, are immunoglobulin molecules and immunologically active fragments of immunoglobulin molecules. Such portions known in the art as Fab, Fab'; F(ab')$_2$ and F$_V$ are included. Typically, antibodies bind ligands that range in size from about 6 to about 34 Å with association constants in the range of about $10^4$ to $10^{10}$ M$^{-1}$ and as high as $10^{12}$ M$^{-1}$. Antibodies may be polyclonal or monoclonal (MoAb). Antibodies can bind a wide range of ligands, including small molecules such as steroids and prostaglandins, biopolymers such as nucleic acids, proteins and polysaccharides, and synthetic polymers such as polypropylene. An "antibody combining site" is that structural portion of an antibody molecule comprised of a heavy and light chain variable and hypervariable regions that specifically binds (immunoreacts with) antigen. The term "immunoreact" in its various forms is used herein to refer to binding between an antigenic determinant-containing molecule and a molecule containing an antibody combining site such as a whole antibody molecule or a portion thereof. An "antigenic determinant" is the actual structural portion of the antigen that is immunologically bound by an antibody combining site. The term is also used interchangeably with "epitope".

Ligand: a molecule that contains a structural portion that is bound by specific interaction with a particular receptor molecule.

Ligand-induced Binding Site (LIBS): a neo-antigenic determinant that is expressed by a cell surface receptor-ligand complex produced by a non-random (specific) binding reaction but not expressed by either the non-occupied receptor or the non-bound ligand. A LIBS can be either "conformational" or "sequential". A LIBS as used herein can be the result of specific alterations of the receptor induced by ligand binding, i.e., a "cryptic antigenic determinant", or it can be formed by a combination of receptor and ligand amino acid residues at a receptor-ligand contact site.

Oligonucleotide or Polynucleotide: a polymer of single or double stranded nucleotides. As used herein "oligonucleotide" and its grammatical equivalents will include the full range of nucleic acids. An oligonucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art.

Polypeptide or Peptide: a linear series of at least two amino acid residues in which adjacent residues are connected by peptide bonds between the alpha-amino group of one residue and the alpha-carboxy group of an adjacent residue.

Protein: refers to a linear series of more than 50 amino acid residues in which adjacent residues are connected via peptide linkages.

Receptor: a biologically active proteinaceous molecule that specifically binds to (or with) other molecules (ligands). Receptors can be glycosylated.

B. Method of Platelet Characterization

The instant methods afford protocols for characterizing platelet adhesion defects in terms of activation, ligand binding, and post-occupancy defects. Based on the model depicted in FIG. 1, abnormal platelet aggregation can arise from a defect in the activation of platelet fibrinogen receptors, a defect in fibrinogen binding per se, or a defect in the postoccupancy events required for optimal aggregation. The usefulness of this model was tested on patients with persistent and severe defects in platelet aggregation. In a preferred embodiment, receptor activation was quantitated using either $^{125}$I-fibrinogen or a fluorescein-labeled MoAb (PAC1) (Shattil et al., *J. Biol. Chem.*, 260:11107 (1985)) which specifically recognizes the activated form of GPIIb-IIIa. The disclosures of all references cited herein are hereby incorporated by reference.

1. Determination of Activation Competence

The instant method in part comprises analyzing a platelet-containing bodily fluid sample taken from a patient for platelets showing activation competence. Useful body fluid samples are typically vascular fluid samples, such as blood and platelet-containing portions of blood, such as platelet-rich plasma and the like. The analysis will preferably employ fluorescence activated flow cytometry to determine the presence of activation competent platelets. Typically, the method will involve admixing the patient's platelet-containing sample with a predetermined amount of a platelet agonist that is sufficient to activate normal platelets. The sample will also be mixed with an activation specific ligand (ASL) that preferentially binds to activated normal platelets. The reaction admixture containing ASL and activated platelets is maintained under predetermined biological assay conditions for a time period sufficient for normal activated platelets to bind with the ASL to form a reaction product. The amount of reaction product is determined, and usually recorded, and is related to the amount of activation competent platelets present in the sample. The amount of product formed can be correlated with predetermined reference values using the assay protocols described herein to identify activation defects.

a. Platelet Agonists: The platelet agonists employed in the present invention "activate" normal target platelets for aggregation by converting the platelets from their normal resting state into a state suitable for subsequent aggregation. The mechanism of activation is not well known and is believed to vary according to the type of agonist used. At least one activation pathway appears to involve G protein-mediated activation of phospholipase C, followed by activation of protein kinase C. Shattil et al., *J. Biol. Chem.*, 261:992 (1987).

The binding of fibrinogen to platelets involves the platelet membrane glycoprotein GPIIb-IIIa. Further, efficient binding of such large ligands as fibrinogen requires activation by suitable agonists. Illustrative agonists include ADP (adenosine diphosphate), thrombin, and the like. Additionally, such agonists as PMA may be employed which directly activate protein kinase C. Other agonists may be employed and are well-known to those skilled in the art. See, e.g., Nurden, et al., *Br J Haematol*, 28:253 (1974); Mustard et al., *Blood*, 54:987 (1979); Bennett et al., *J. Clin. Invest.*, 64:1393 (1979); Marguerie et al., *J. Biol. Chem.*, 254:5357 (1979). The agonists used herein are believed to work by causing the ligand binding pocket of GPIIb-IIIa to open up thereby allowing increased accessibility of large ligands to the ligand binding site (FIG. 1).

b. Activation Specific Ligands: An "activation specific ligand" (ASL) as used herein is a molecule that specifically binds an activated receptor molecule. As used herein, the term "specific binding" and its grammatical equivalents refers to a non-random binding reaction between a cell surface receptor and a ligand molecule. Illustrative of a specifically-bound receptor-ligand complex as contemplated herein is that between activated platelet GPIIb-IIIa and fibrinogen at the platelet surface. Other ligands known to specifically bind activated GPIIb-IIIa include the MoAb PAC-1 and functional equivalents thereof [Shattil et al., *J. Biol. Chem.*, 260:11107 (1985)], fibronectin, vitronectin, and von Willebrand factor. Thus, suitable ligands include native ligands for activated GPIIb-IIIa and antibodies raised against antigenic determinants of GPIIb-IIIa.

The instant ASL molecules additionally bind preferentially to activated platelets. As used herein, a reagent molecule of the instant invention is regarded as "preferentially binding" a target species in the assay when the reagent more strongly associates with the target molecule than with other species present in the assay. Thus, the reaction of reagent molecule with target generally will have a greater association constant than the reaction of reagent with any other species present in the assay. Typically, a reagent herein will "preferentially" bind its target species, e.g., an ASL will bind an activated integrin, when the binding affinity of the reagent for target is 2-3 fold greater, and preferably at least 10 times greater, than the corresponding affinity of the reagent for another species, e.g., unactivated integrin.

The relative binding affinity of a reagent molecule for its target species is conveniently determined as described herein using the method of fluorescence activated flow cytometry. Accordingly, a labelled ASL suitable for use herein will show an increase in the mean cell fluorescence intensity (MCFI) of a normal platelet sample when the sample undergoes activation. The increase in MCFI will typically be greater than about two-fold, and preferably greater than about ten-fold, of the MCFI for an unactivated normal platelet sample.

An antibody ASL of the present invention is characterized as containing antibody molecules that immunoreact with activated GPIIb-IIIa but do not preferentially bind (immunoreact) with unactivated GPIIb-IIIa. In a preferred embodiment, the antibody molecules immunoreact with either the GPIIIa or GPIIb chains of the integrin. Usually, the antibodies will also bind to the ligand binding site of GPIIb-IIIa, as the ligand binding site will be proximal to those amino acid residues most affected by the activation process. In another preferred embodiment, an antibody composition of this invention has more than one species of paratope capable of immunoreacting with activated GPIIb-IIIa.

The preferred ASL antibody as contemplated herein is typically produced by immunizing a mammal with an inoculum containing platelets from a preselected host animal, thereby inducing in the mammal antibody molecules having the appropriate immunospecificity for GPIIb-IIIa molecules on the platelets. The antibody molecules are then collected from the mammal and screened to the extent desired by well known techniques such as, for example, by immunoaffinity for stimulated platelets. The antibody composition so produced can be used inter alia, in the diagnostic methods and systems of the present invention to detect activated platelets in a bodily fluid sample.

An anti-activated GPIIb-IIIa monoclonal antibody (MoAb) is also contemplated by the present invention. The phrase "monoclonal antibody composition" in its various grammatical forms refers to a population of antibody molecules that contain only one species of antibody combining site capable of immunoreacting with a particular antigen. The instant MoAb composition thus typically displays a single binding affinity for any antigen with which it immunoreacts. A monoclonal antibody composition may therefore contain an antibody molecule having a plurality of antibody combining sites, each immunospecific for a different antigen, e.g., a bispecific monoclonal antibody.

An instant MoAb is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. Such antibodies were first described by Kohler and Milstein, *Nature* 256:495–497 (1975), which description is incorporated by reference.

A monoclonal antibody can also be produced by methods well known to those skilled in the art of producing chimeric antibodies. Those methods include isolating, manipulating, and expressing the nucleic acid that codes for all or part of an immunoglobulin variable region including both the portion of the variable region comprising the variable region of immunoglobulin light chain and the portion of the variable region comprising the variable region of immunoglobulin heavy chain. Methods for isolating, manipulating, and expressing the variable region coding nucleic acid in procaryotic and eucaryotic hosts are disclosed in Robinson et al., PCT Publication No. WO 89/0099; Winter et al., European Patent Publication No. 0239400; Reading, U.S. Pat. No. 4,714,681; Cabilly et al., European Patent Publication No. 0125023; Sorge et al., *Mol. Cell Biol.*, 4:1730–1737 (1984); Beher et al., *Science*, 240:1041–1043 (1988); Skerra et al., *Science*, 240:1030–1041 (1988); and Orlandi et al., *Proc. Natl. Acad. Sci., U.S.A.*, 86: 3833–3837 (1989). Typically the nucleic acid codes for all or part of an immunoglobulin variable region that binds a preselected antigen (ligand). Sources of such nucleic acid are well known to one skilled in the art and, for example, may be obtained from a hybridoma producing a monoclonal antibody that binds the preselected antigen, or the preselected antigen may be used to screen an expression library coding for a plurality of immunoglobulin variable regions, thus isolating the nucleic acid.

These preferred monoclonal antibodies immunoreact with free activated GPIIb-IIIa or with GPIIb-IIIa present in a receptor-ligand complex. The antibodies also can immunologically react with platelet-associated GPIIb-IIIa unbound with ligand or bound with a ligand, such as fibrinogen. Representative of a monoclonal antibody of this type is the PAC-1 antibody.

The present invention contemplates a method of forming a monoclonal antibody molecule that immunoreacts with an activated region of GPIIb-IIIa, i.e., a region that has a different three-dimensional structure than when the integrin is in its resting conformation. The method comprises the steps of:

(a) Immunizing an animal with a cell surface-receptor-ligand complex. Preferably, the immunogen is a homologous sample of platelets taken from a subject animal species. However, the antigen may also be linked to a carrier protein such as keyhole limpet hemocyanin, particularly when the antigen is small. The immunization is typically accomplished by administering the sample to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the receptor.

(b) A suspension of antibody-producing cells removed from the immunized mammal is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3X63-Ag8.653, Sp2/0-Ag14 and the like.

In preferred embodiments, treatment with the transforming agent results in the production of an "immortalized" hybridoma by means of fusing the suspended spleen cells with mouse myeloma cells from a suitable cell line, e.g., SP-2, by the use of a suitable fusion promoter. The preferred ratio is about 5 spleen cells per myeloma cell in a suspension containing about $10^8$ splenocytes. A preferred fusion promoter is polyethylene glycol having an average molecule weight from about 1000 to about 4000 (commercially available as PEG 1000, etc.); however, other fusion promoters known in the art maybe employed.

The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody. In certain cases, however, secreting myeloma lines may be preferred.

(d) The transformed cells are then cloned, preferably to monoclonality. The cloning is preferably performed in a tissue culture medium that will not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not sustain the unfused myeloma cells. The cells are cultured in this medium for a time sufficient to allow death of the unfused cells (about one week). The dilution can be a limiting dilution, in which the volume of diluent is statistically calculated to isolate a certain number of cells (e.g., 1–4) in each separate container (e.g., each well of a microtiter plate). The medium is one (e.g., HAT medium) that will not sustain the drug-resistant (e.g., 8-azaguanine resistant) unfused myeloma cell line.

(e) The tissue culture medium of the cloned transformants is analyzed (immunologically assayed) to detect the presence of antibody molecules that preferentially react with GPIIb-IIIa on activated platelets. This is accomplished using well known immunological techniques.

(f) A desired transformant is then selected and grown in an appropriate tissue culture medium for a suitable length of time, followed by recovery (harvesting) of the desired antibody from the culture supernatant by well known techniques. The suitable medium and suitable length of culturing time are also well known or are readily determined.

To produce a much greater concentration of slightly less pure monoclonal antibody, the desired hybridoma can be transferred by injection into mice, preferably syngenic or semisyngenic mice. The hybridoma will cause formation of antibody-producing tumors after a suitable incubation time, which will result in a high concentration of the desired antibody (about 5–20 mg/ml) in the bloodstream and peritoneal exudate (ascites) of the host mouse.

Media and animals useful for the preparation of these compositions are both well known in the art and commercially available and include synthetic culture media, inbred mice and the like. An exemplary synthetic medium is Dulbecco's minimal essential medium [DMEM; Dulbecco et al., *Virol.* 8:396 (1959)] supplemented with 4.5 gm/l glucose, 20 mM glutamine, and 20% fetal calf serum. An exemplary inbred mouse strain is the Balb/c.

The monoclonal antibodies produced by the above method can be used, for example, in diagnostic and therapeutic modalities wherein formation of an activation competent platelet immunoreaction product is desired. Methods for producing hybridomas that generate (secrete) antibody molecules having a desired immunospecificity, i.e., having the ability to immunoreact with a particular protein, an identifiable epitope on a particular protein and/or a polypeptide, are well known in the art and are described further herein. Particularly applicable is the hybridoma technology described by Niman et al., *Proc. Natl. Acad. Sci. USA*, 80:4949–4953 (1983), and by Galfre et al., *Meth. Enzymol.*, 73:3–46 (1981), which descriptions are incorporated herein by reference.

A further preferred method for forming the instant antibody compositions involves the generation of libraries of Fab molecules using the method of Huse et al., *Science*, 246:1275 (1989). In this method, mRNA molecules for heavy and light antibody chains are isolated from the immunized animal. The mRNAs are amplified using polymerase chain reaction (PCR) techniques. The nucleic acids are then randomly cloned into lambda phages to generate a library of recombined phage particles. The phages can then be used to infect an expression host such as *E. coli*. The *E. coli* colonies and corresponding phage recombinants can then be screened for those producing the desired Fab fragments.

The antibody molecule-containing compositions employed in the present invention can take the form of solutions or suspensions. The preparation of a composition that contains antibody molecules as active ingredients is well understood in the art. Typically, such compositions are prepared as liquid solutions or suspensions, however, solid forms suitable for solution in, or suspension in, liquid can also be prepared. The preparation can also be emulsified. The active therapeutic ingredient is often mixed with excipients which do not interfere with the assay and are compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents and the like which enhance the effectiveness of the active ingredient.

An antibody molecule composition can be formulated into a neutralized acceptable salt form. Acceptable salts include the acid addition salts (formed with the free amino groups of the antibody molecule) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

2. Determination of Ligand-Occupancy Competence

The present invention also contemplates determining the presence of ligand-occupancy competent platelets in a platelet-containing body fluid sample. The determination of ligand-occupancy competence may be made by determining the ligand binding ability of activated receptors or may be made by determining the ligand binding ability of receptors independent of activation. In the latter case, an activation-independent ligand (AIL) will be employed to react with membrane-bound platelet receptors.

The determination of ligand-occupancy competence will typically comprise admixing a platelet sample with a predetermined amount of an AIL that is sufficient to form a ligand-induced binding site (LIBS) on normal platelets. The LIBS may be probed with an anti-LIBS antibody composition that immunoreacts with the LIBS. The LIBS may be localized on the platelet receptor or may extend onto the surface of the ligand as well. A determination of whether the LIBS is localized only on the receptor can simply be made by changing the ligand so that a different epitope is presented to the anti-LIBS antibody. In order to be a suitable probe of a LIBS, an anti-LIBS antibody will immunoreact with the LIBS but not react substantially with free AIL or with platelets that are not bound to ligand, i.e., resting or activated but unoccupied platelets.

In another embodiment, ligand-occupancy competence will be determined in activation competent platelets. The method will comprise admixing a body fluid sample with a predetermined amount of platelet agonist that is sufficient to activate normal platelets. Also, an activation specific ligand (ASL) will be admixed with the sample in which the ASL binds activated platelets as described above to form a LIBS. In addition, an anti-LIBS antibody, as described herein, will be admixed with the sample to afford detection of the presence of LIBS, thereby indicating ligand-occupancy competence in the platelets. The reaction admixture so formed will be maintained as described herein to form an amount of immunoreaction product that is related by predetermined criteria to an amount of ligand-occupancy competent platelets.

Preferably, the detection of LIBS in the present invention will be afforded by the method of fluorescence activated flow cytometry. Accordingly, a labelled anti-LIBS antibody suitable for use herein will show an increase in the mean cell fluorescence intensity (MCFI) of a normal platelet sample exhibiting the LIBS versus a sample that does not show a LIBS, e.g., platelets unoccupied by an AIL. The increase in MCFI will typically be greater than about two-fold, and preferably greater than about ten-fold, of the MCFI for a platelet sample not exhibiting a LIBS, i.e., not exposed to added AILs.

a. Activation Independent Ligands: An instant activation independent ligand (AIL) will be a molecule that binds to platelets independent of their activation. The AIL typically will be a small polypeptide molecule that binds to platelets, e.g., in the peptide binding region of GPIIb-IIIa receptors. The occupation of such a binding site may be probed directly by determining the inhibition exerted by the AIL on other competing ligands, e.g., ASLs. Alternatively, ligand occupancy of the binding region may be determined indirectly by probing for a LIBS as described herein.

As mentioned, the subject AIL polypeptide may include an amino acid residue sequence that has the capacity to inhibit platelet adhesion, e.g., by binding to GPIIb-IIIa. Particularly preferred platelet adhesion-inhibiting polypeptides include the amino acid residue sequence RGD, such as those described in U.S. Pat. Nos. 4,683,291, and 4,578,079. A particularly preferred RGD-containing peptide is GRGDSP.

Amino acid residues present in a subject polypeptide, in addition to a sequence corresponding to an above-described formula, can be any residues that do not materially affect the basic and novel characteristics of the polypeptide, as are discussed herein. Such additional residues are usually added to one or both termini of an enumerated peptide and can include repeats and partial repeats of an enumerated peptide sequence or contiguous residues of the polypeptide sequence. A preferred polypeptide will include an RGD sequence. Thus, a polypeptide of the present invention need not be identical to the amino acid residue sequence of polypeptides presented herein, so long as it is able to exhibit at least one of the above preferred characteristics of a subject polypeptide, namely, binding to unactivated platelets or inhibiting ASLs. Therefore, a subject polypeptide can be subject to various changes, such as insertions, deletions and substitutions, either conservative or non-conservative, where such changes provide for certain advantages in their use.

Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity.

When a polypeptide of the present invention has a sequence that is not identical to a preferred sequence because one or more conservative or non-conservative substitutions have been made, usually no more than about 20% and more usually no more than 10% of the amino acid residues are substituted. An exception is where additional residues have been added at either terminus for the purpose of providing a "linker" by which the polypeptides of this invention can be conveniently affixed to a label or solid matrix, or antigenic carrier. Labels, solid matrices and carriers that can be used with the polypeptides of this invention are described hereinafter.

Amino acid residue linkers are usually at least one residue and can be 40 or more residues, more often 1 to 10 residues. Typical amino acid residues used for linking are tyrosine, cysteine, lysine, glutamic and aspartic acid, or the like. A representative linker is a Cys-Gly-Gly (CGG-) tripeptide attached to the amino terminus of a subject polypeptide by the carboxy terminal glycine residue of the linker. In addition, a polypeptide sequence of this invention can differ from the natural sequence by the sequence being modified by terminal-$NH_2$ acylation, e.g., acetylation, or thioglycolic acid amidation, terminal-carboxlyamidation, e.g., ammonia, methylamine, etc.

A subject polypeptide can be synthesized by any techniques that are known to those skilled in the polypeptide art. An excellent summary of the many techniques available may be found in J. M. Steward and J. D. Young, "Solid Phase Peptide Synthesis", W. H. Freeman Co., San Francisco, 1969, and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis.

A related embodiment contemplates a composition for promoting the attachment (adhesion) of cells to a substrate. Based on the ability of a subject polypeptide to bind to platelets, the subject polypeptide can be used to promote cell attachment activity when the polypeptide is immobilized onto a substrate.

A composition containing a subject polypeptide is used to treat a substrate and thereby to immobilize the polypeptide contained in the composition onto the substrate. The substrate can be any surface on which cell adhesion promoting activity is desired and includes containers for cell culture, medical devices, a prosthetic device, a synthetic resin fiber, a blood vessel or vascular graft, a percutaneous device, artificial organs and the like. The surface can be comprised of glass, a synthetic resin, nitrocellulose, polyester, agarose, collagen or a long chain polysaccharide.

Immobilization of polypeptides onto substrate can be accomplished by a variety of means and depends, inter alia, on the substrate and the mechanism of immobilization desired. Methods for polypeptide immobilization or coupling are well known in the art and typically involve covalent linkages between a thiol or amino group on the polypeptide to a reactive group present on the substrate. For exemplary polypeptide immobilization methods see Aurameas et al., Scand J. Immunol., Vol. 8 Suppl. 7:7-23 (1978); U.S. Pat. Nos. 4,493,795, 4,578,079 and 4,671,950; Klipstein et al., J. Infect. Dis., 147:318-326 (1983) and Liu et al., Biochem., 80:690 (1979). For examples of the use of cell adhesion promoting polypeptides see U.S. Pat. No. 4,578,079.

b. Anti-LIBS Antibodies: The presence of ligand-occupancy competent platelets in a fluid sample will generally be detected through the use of anti-LIBS antibodies. These antibodies immunoreact with epitopes on the platelets that are generated upon receptor-ligand complex formation. Thus, the antibodies will not substantially react with platelets absent complex formation nor will they react with unbound ligand. The epitopes generated upon complex formation can be localized on the receptor, ligand, or both. The exact binding site(s) of the anti-LIBS antibodies to the complex can be probed by such techniques as NMR, x-ray crystallography, immunoadsorption chromatography using mutant receptors, and cross-linking reactions between receptor and ligand.

The instant anti-LIBS antibodies may be polyclonal or monoclonal species and may be prepared using such techniques as described above for ASLs. The preparation and properties of anti-LIBS antibodies are discussed more fully in U.S. Ser. No. 07/417,565, filed on Oct. 5, 1989 which disclosure is incorporated herein by reference.

In a preferred embodiment, the anti-LIBS antibodies will be monoclonal, such as the antibody generated by the PMI-1 hybridoma, which immunoreacts with a LIBS on the GPIIb-IIIa adhesin. Chemical cross-linking studies have recently localized the LIBs of GPIIb-IIIa to the alpha (GPIIb) subunit of the integrin at a location proximal to the calcium binding site. D'Souza et al. J. Biol. Chem., 265:3440 (1990). LIBs have also been detected on the vitronectin receptor suggesting the generation of LIBs upon complex formulation is a common property of many integrin receptors. Ginsberg et al., J. Biol. Chem., 262:5437 (1987).

A further means of detecting ligand binding competent platelets will employ antibodies to receptor-induced binding sites (RIBS) on the ligand for the receptor. Since ligand binding competence may be inferred by the generation of receptor-induced sites on the ligand, this method detects receptor/ligand complex formation. Anti-RIBS antibodies are further discussed in Zamarron et al. Blood 74:208a (Suppl. 1) (1989).

3. Correlation of Results—Identification of Post-occupancy Defects

The results of the analyses for activation competent and ligand-binding competent platelets will be compared with predetermined criteria for assessing the presence of defects. Thus, the amount of activation competent platelets determined will be compared with a predetermined threshold level of such platelets below which a deficiency is indicated. Such reference level of competent platelets is determined usually prior to the assay using selected reaction conditions, e.g., pH, temperature, reaction times, etc., described more fully herein. The reaction conditions used will ordinarily be optimized to maximize the indication of activation in normal platelets. The actual measurement of platelets may be expressed in any convenient form, e.g., weight, cell number, concentration, etc.

Similarly, the amount of ligand-occupancy competent platelets will be determined using predetermined reaction conditions. The amount of competent platelets ascertained will be correlated with a predetermined competency level to determine whether the amount of competent platelets is less than the threshold level for defect indication. A defect in ligand binding is indicated if the presence of platelets is less than the predetermined level.

When gross platelet adhesion dysfunction is indicated, e.g., by aggregometry, indications of sufficient amounts of activation and ligand-binding competent platelets allow identification of a post-occupancy defect.

C. Diagnostic Systems

Also contemplated in the instant invention are diagnostic kits for performing the described platelet characterizations. A diagnostic system in kit form of the present invention includes, in an amount sufficient for at least one assay, a composition containing antibody or monoclonal antibody molecules or fragments thereof of the present invention, as a separately packaged reagent, together with a label that indicates the presence of an immunoreaction product. Instructions for use of the packaged reagent are also typically included. "Instructions for use" typically include a tangible expression describing the reagent concentration or at least one assay method parameter such as the relative amounts of reagent and sample to be admixed, maintenance time periods for reagent/sample admixtures, temperature, buffer conditions and the like. In one embodiment, a diagnostic system is contemplated for assaying for the presence of activated platelets and for a receptor-ligand complex, in a complex-containing vascular fluid sample, such as blood or plasma.

The kit is provided as an enclosure, (package) that comprises a container for ASL molecules that react with activated platelets. Typically, the kit will also contain a platelet agonist for stimulating normal platelets into their activated states. Exemplary agonists include ADP and thrombin, while the ASL molecules will be PAC-1 antibodies.

The kit also comprises a container for AIL molecules that bind with receptors on the platelets to form LIBS on the receptor. A preferred AIL compound is GRGDSP.

Also, the diagnostic system comprises a container for anti-LIBS antibody molecules that immunoreact with a LIBS present on a receptor-ligand complex. A preferred anti-LIBS antibody is PMI-1. Further preferred are kits wherein the antibody molecules are linked to a radionuclide label, preferably $^{125}$I-labeled antibody molecules.

An in vitro diagnostic system of the present invention includes a label or indicating means capable of signaling the formation of a specificity bound complex containing an antibody molecule of the present invention. As used herein, the terms "label" and "indicating means" in their various grammatical forms refer to single atoms and molecules that are either directly or indirectly involved in the production of a detectable signal to indicate the presence of a complex. Exemplary labels include $^{111}$In, $^{99}$Tc, $^{67}$Ga, and $^{132}$I and nonradioactive labels such as biotin and enzyme-linked antibodies. Any label or indicating means can be linked to or incorporated in an antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel methods and/or systems.

The linking of labels to polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8, Suppl. 7:7–23 (1978), Rodwell et al., *Biotech.*, 3:889–894 (1984), and U.S. Pat. No. 4,493,795.

The diagnostic systems can also include a specific binding agent. A "specific binding agent" is a chemical species capable of selectively binding a reagent species of the present invention but is not itself an antibody molecule of the present invention. Exemplary specific binding agents are antibody molecules, complement proteins or fragments thereof, protein A and the like which immunoreact with an antibody molecule of this invention when it is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a complex containing one of the instant reagents.

For example, the diagnostic kits of the present invention can be used in an "ELISA" format to detect the presence or quantity of fibrinogen-bound platelets in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; No. 3,850,752; and No. 4,016,043, which are all incorporated herein by reference.

In preferred embodiments, the antibody or antigen reagent component can be affixed to a solid matrix to form a solid support that is separately packaged in the subject diagnostic systems. The reagent is typically affixed to the solid matrix by adsorption from an aqueous medium, although other modes of affixation, well known to those skilled in the art, can be used. Useful solid matrices are well known in the art. Such materials include the cross-linked dextran available under the trademark SEPHADEX from Pharmacia Fine Chemicals (Piscataway, N.J.); agarose; polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like. Usually, the reagents will be packaged under an inert atmosphere.

D. Assay Methods

The present invention contemplates any method that results in detecting an ASL or a LIBS on a cell surface receptor-ligand complex. Preferably the ASL binds to activated GPIIb-IIIa and the LIBS is expressed in response to the binding of a ligand to GPIIb-IIIa.

The relative binding affinity of a reagent molecule for its target species is conveniently determined as described herein using the method of fluorescence activated flow cytometry. Thus, an activation defect will be indicated whenever the mean cell fluorescence intensity (MCFI) of a platelet-containing sample from a patient suspected of having the defect is less than about 50%, and preferably less than about 10%, of the MCFI of a normal platelet sample.

The method for detecting a LIBS comprises the formation of an immunoreaction product between a LIBS and an anti-LIBS antibody molecule, as disclosed herein, and the subsequent detection of the immunoreaction product so formed. The LIBS to be detected can be present in a vascular fluid sample, such as a blood sample containing platelets, or can be present in a body tissue. Those skilled in the art will understand that there are numerous well known clinical diagnostic chemistry procedures that can be utilized to form detectible immunocomplexes. Thus, while exemplary assay methods are described herein, the invention is not so limited.

A particularly preferred assay method employs fluorescence activated flow cytometry to detect a LIBS. Accordingly, a ligand binding defect will be indicated whenever the MCFI of a platelet-containing sample from a patient suspected of having the defect is less than about 50%, and preferably less than about 10%, of the MCFI of a normal platelet sample, using the assay methods described herein.

Various heterogeneous and homogeneous assay protocols can be employed, either competitive or non-competitive for detecting the presence and preferably amount of fibrinogen-bound platelets in a platelet-containing body sample, preferably a body fluid sample, more preferably a vascular fluid sample such as blood or a platelet-containing portion of blood. The method involves the admixture of a platelet-containing blood sample with antibody molecules that immunoreact with platelet GPIIb-IIIa. The immunoreaction admixture thus formed is maintained under biological assay conditions for a time period sufficient for any fibrinogen-bound platelets to immunoreact with the labeled antibodies and form a labeled immunoreaction product. The labeled immunoreaction products are then separated from the non-reacted labeled-antibodies, typically by centrifugation sufficient to pellet all platelets present in the sample. The amount of labeled immunoreaction product formed is then assayed.

Biological assay conditions are those that maintain the biological activity of the antibody molecules and polypeptide molecules of this invention and the fibrinogen-bound platelets sought to be assayed. Those conditions include a temperature range of about 4 degrees C. (4° C.) to about 45° C., preferably about 37° C., at a pH value range of about 5 to about 9, preferably about 7, and an ionic strength varying from that of distilled water to that of about one molar sodium chloride, preferably about that of physiological saline. Methods for optimizing such conditions are well known in the art.

Insofar as various drugs, such as the synthetic peptide GRGDSP or the snake venom peptide trigramin, can be used to modulate platelet function by complexing GPIIb-IIIa via the binding site for RGD-containing ligands, the present invention also contemplates methods to detect the degree of occupancy of the ligand binding site by the drug on GPIIb-IIIa. The method is practiced essentially as described above for detecting fibrinogen-bound platelets, except that an RGD-containing ligand analog, and not fibrinogen, has bound the platelets. The method is practiced to quantitate the amount of analog (drug) bound, i.e., the degree of occupancy of the RGD-ligand binding site.

The ability of platelets to bind fibrinogen and/or to express a LIBS can be monitored in a diagnostic method of the present invention. A platelet-containing body fluid sample is admixed and incubated with a GPIIb-IIIa specific ligand such as fibrinogen or a synthetic peptide such as GRGDSP, or with other GPIIb-IIIa specific ligands such as the fibrinogen gamma chain polypeptide (Fb gamma 400-411), for a time period sufficient for the ligand to bind to and form a complex with GPIIb-IIIa-containing receptor on the platelet surface. The amount of ligand admixed is an amount sufficient to saturate the GPIIb-IIIa specific LIBS present on the platelets in the body sample. The formation of the GPIIb-IIIa complex results in the expression of LIBS on GPIIIa in normal platelets.

In a preferred embodiment, a blood sample to be analyzed is withdrawn from a patient and apportioned into aliquots. At least one aliquot is used for the determination of activation competence and at least one aliquot is used for the ligand-binding competence analysis. The analysis can be performed concurrently but usually will be performed sequentially. When the analyses are performed sequentially, the ligand-binding competence measurement may be performed prior to or subsequent to the activation competence analysis.

In a preferred embodiment, data obtained in the instant activation and ligand-occupancy competency analyses will be recorded via a tangible medium, e.g., computer storage or hard copy versions. The data may be automatically input and stored by standard A/D instrumentation that is commercially available. Also, the data may be recalled and reported or displayed as desired for best presenting the instant correlations of data. Accordingly, instrumentation and software suitable for use with the present methods are contemplated as within the scope of the present invention.

The present invention is more fully understood by the specific examples described hereinbelow and by the appended claims.

EXAMPLES

The following examples illustrate, but do not limit, the present invention.

Based on the model depicted in FIG. 1, abnormal platelet aggregation can arise from a defect in the activation of platelet fibrinogen receptors, a defect in fibrinogen binding per se, or a defect in the postoccupancy events required for optimal aggregation. The potential usefulness of this model was tested by studying two patients with persistent and severe defects in platelet aggregation. To quantitate fibrinogen receptor activation and ligand binding, a fluorescein-labeled MoAb (PAC1) which specifically recognizes the activated form of GPIIb-IIIa, was employed (Shattil et al., *J. Biol. Chem.*, 260:11107 (1985)). Antibody binding was measured in small (5 μL) samples of platelet rich plasma by flow cytometry.

1. Antibodies of the Present Invention

Preparation and characterization of the antibodies used herein have been described in detail elsewhere and their properties are listed in Table 1. Methods for preparing and screening the antibodies listed in Table 1 are described in the following references: PAC-1: Shattil et al., *J. Biol. Chem.*, 260:11107 (1985); PMI-1: Frelinger et al., *J. Biol. Chem.*, 263:12397 (1988), Loftus et al., *Proc. Natl. Acad. Sci. USA*, 840:7114 (1987); Anti-LIBS 1 and Ab15: Frelinger et al., *J. Biol. Chem.* 265:6346 (1990); Tab: McEver et al., *J. Biol. Chem.*, 258:5269 (1983); 4F10: Woods et al., *J. Biol. Chem.*, 261:15242 (1986); 10E5: Coller et al., *J. Clin. Invest.*, 72:325 (1983); 7E3: Coller et al., *J. Clin Invest.*, 76:901 (1985); A2A9: Gartner et al., *Blood*, 66:305a (1985), Bennett et al., *Proc. Natl. Acad. Sci. USA*, 80:2417 (1983); TSPI-1: Aiken et al., *Blood*, 69:58 (1987). Fluorescein isothiocyanate-conjugated antibodies were prepared as described to achieve fluorescein/protein molar ratios of 3:6 (Shattil et al., *Blood*, 70:307 (1987)).

TABLE 1

| MONOCLONAL ANTIBODIES USED | | | |
|---|---|---|---|
| Antibody | Specificity | Fibrinogen Binding[b] | Effect of Peptides[c,d] |
| PAC 1 | GPIIb-IIIa[a] on activated platelets | Decrease | Decrease |
| PMI-1 | GPIIb heavy chain (C-Terminus) | None | Increase |
| LIBS1 | GPIIIa | None | Increase |
| Ab 15 | GPIIIa | None | None |
| Tab | GPIIb | None | None |
| 4F10 | GPIIb-IIIa | Decrease | N.D. |
| 10E5 | GPIIb-IIIa | Decrease | N.D. |
| 7E3 | GPIIb-IIIa | Decrease | N.D. |
| A2A9 | GPIIb-IIIa | Decrease | RGD = None gamma(402-411) = Decrease |
| Anti-TSP | Thrombospondin | None | None |

[a]GPIIb-IIIa Complex
[b]Effect of antibody on fibrinogen binding to platelets
[c]Effect of RGD or fibrinogen gamma chain, C-terminal peptides on antibody binding
[d]N.D. = Not Determined

2. Peptides of the Present Invention

Peptides were synthesized using an Applied Biosystems (Mountain View, Calif.) peptide synthesizer and methods recommended by the manufacturer. Peptides were more than 90% homogeneous by high performance liquid chromatography, and amino acid compositions were consistent with the desired sequence. The peptides were Gly-Arg-Gly-Asp-Ser-Pro (GRGDSP), fibrinogen gamma(402-411)=Leu-Gly-Gly-Ala-Lys-Gln-Ala-Gly-Asp-Val (LGGAKQAGDV), Lys-Tyr-Gly-Arg-Gly-Asp-Ser (KYGRGDS), and by Lys-Gln-Ala-Gly-Asp-Val (KQAGDV).

3. Analysis of Platelet Surface GPIIb-IIIa by Flow Cytometry

Platelet rich plasma was obtained by taking venous blood from patients and controls who had not ingested medications for at least 10 days, anticoagulating with 1/10 volume of 3.8% sodium citrate, and sedimentating red and white blood cells at 180 g for 20 minutes at room temperature. Immediately thereafter, 5-μL aliquots of platelet-rich plasma were added to polypropylene tubes containing a fluorescein isothiocyanate-conjugated monoclonal antibody ($10^{-9}$ to $10^{-6}$ mol/L) in Tyrode's buffer (1% bovine serum albumin, 2 mmol/L $MgCl_2$, 137.5 mmol/L NaCl, 12 mmol/L $NaHCO_3$, 2.6 mmol/L KCl, pH 7.4). See FIG. 2. Samples were incubated without stirring in a total volume of 50 μL for 15 minutes at room temperature with agonists and peptides as indicated. Samples were then diluted to 0.5 mL with Tyrode's buffer and analyzed on a FACStar flow cytometer (Bectin-Dickinson Immunocytometry Systems, Mountain View, Calif.). Light scatter and fluorescence signals were acquired at logarithmic gain, and 10,000 platelets in each sample were analyzed. Results are expressed as mean platelet fluorescence intensity in arbitrary fluorescence units or as histograms of log platelet fluorescence intensity in arbitrary units on the abscissa and platelet number on the ordinate.

The Cam Variant of Thrombasthenia is due to a Defect in Ligand Recognition

The Cam variant of Glanzmann's thrombasthenia is characterized by markedly reduced fibrinogen binding to platelets that contain near normal quantities of GPIIb-IIIa (Ginsberg et al., *J. Clin. Invest*, 78:1103 (1986)). The presence of GPIIb-IIIa on the Cam platelet surface was confirmed by flow cytometry, in which there was comparable binding of an anti-GPIIb MoAb(-Tab) and an anti-GPIIIa MoAb (AB-15) to Cam and normal platelets. In addition, four MoAbs specific for the GPIIb-IIIa complex (A2A9, 7E13, 10E5, 4F10), all of which recognize the nonactivated form of GPIIb-IIIa at 1:1 stoichiometry and inhibit fibrinogen binding to platelets, also bound in comparable amounts to the Cam and normal platelets (FIG. 2); McEver et al., *J. Biol. Chem.* 258:5269 (1983); Woods et al., *J. Biol. Chem*, 258:5269 (1983); Coller et al., *J. Clin. Invest*, 73:325 (1983); Coller et al., *J. Clin. Invest*, 6:101 (1985); Gartner et al., *Blood*, 66:305a (1985). In sharp contrast, there was a complete lack of binding of the activation-specific MoAb PAC1 to ADP-activated Cam platelets (FIG. 2). This defect was not specific to ADP stimulation, because Cam platelets activated with 50 nmol/L phorbol myristate acetate (PMA) also showed no increase in PAC1 fluorescence (not shown).

Since PAC1 may recognize the ligand binding site in GPIIb-IIIa the absence of PAC1 binding could be due to a lack of GPIIb-IIIa activation, a defect in ligand binding, or both (Shattil et al., *J. Biol. Chem.* 260:11107 (1985); Shattil et al., *Blood*, 68:1224 (1986); Taub et al., *J. Biol. Chem.* 264:259 (1989)). To distinguish these possibilities, the observation that small fibrinogen-mimetic peptides bind to GPIIb-IIIa in an activation-independent manner was exploited (Lam et al., *J. Biol. Chem.*, 262:947 (1987); Frelinger et al., *J. Biol. Chem.*. 263:12397 (1988)). The binding of one such peptide (GRGDSP) was assayed by use of PMI-1 and anti-LIBS1 MoAbs, which preferentially recognize GPIIb-IIIa in a 1:1 stoichiometry following the binding of either fibrinogen or small peptide ligands (Frelinger et al., *J. Biol. Chem.*, 263:12397 (1988)). Platelets from a normal individual showed a 2.5-fold increase in PMI-1 binding in the presence of 200 μmol/L GRGDSP (mean fluorescence intensity of untreated platelets=60 arbitrary fluorescence units; GRGDSP- treated platelets=151 fluorescence units). In contrast, Cam platelets showed no increase in PMI-1 binding in response to GRGDSP (mean fluorescence intensity of untreated platelets=102 fluorescence units; GRGDSP-treated platelets=107 fluorescence units) (FIG. 2).

It should be noted that PMI-1 binding to untreated Cam platelets was higher than normal suggesting that the binding of PMI-1 could not be used as a reliable indicator of the binding of GRGDSP to Cam platelets. However, the anti-LIBS1 antibody was more informative in this regard. As shown in FIG. 2, untreated Cam platelets bound less anti-LIBS1 than control platelets (mean fluorescence of 27 and 58 U, respectively). The fibrinogen-mimetic peptide, GRGDSP, caused a four-fold increase in anti-LIBS1 binding to normal platelets (mean fluorescence, 205 U); however, no increase in antibody binding was observed in Cam platelets (mean fluorescence, 25 U). Anti-LIBS1 binding to Cam platelets also failed to increase when platelets were treated With another fibrinogen-mimetic peptide gamma(402-411) (400 μmol/L), instead of GRGDSP (control platelets, 201 fluorescence U; Cam platelets, 31 U) (Kloczewiak et al., *Biochem. Biophys. Res. Commun.*, 107:181 (1982); Plow et al., *J. Biol. Chem.* 259:5388 (1984)).

When anti-LIBS1 binding was examined over a range of GRGDSP peptide concentrations, control platelets showed a saturable increase in antibody binding such that half-maximal expression of the LIBS1 epitope on GPIIIa was observed at 20 μmol/L peptide. This is similar to the IC$_{50}$ of this peptide for fibrinogen binding to activated platelets (Plow et al., *Proc. Natl. Acad. Sci. USA.* 82:8057 (1985)). In contrast, at 200 μmol/L GRGDSP, anti-LIBS1 binding to Cam platelets was less than that seen with control platelets in the presence of 1 μmol/L peptide, suggesting that the affinity of Cam GPIIb-IIIa for this peptide was at least 200-fold less than normal GPII-IIIa. See Table 2.

TABLE 2

RELATIONSHIP BETWEEN GRGDSP PEPTIDE DOSE AND LIBS-1 EXPRESSION IN NORMAL AND CAM PLATELETS*

| [GRGDSP](μM) | Fluorescence Increase | |
|---|---|---|
| | Normal | Cam |
| 2 | 20 | 3 |
| 4 | 31 | 3 |
| 10 | 48 | 3 |
| 40 | 70 | 3 |
| 200 | 106 | 6 |

*Anti-LIBS 1 binding was determined in the presence of the indicated concentrations of the GRGDSP peptide.

4. Isolation and surface radioiodination of platelets

The foregoing data, by use of conformation-specific antibodies and intact cells indicated that the Cam variant was due at least in part to a deficit in ligand recognition by GPIIb-IIIa. To directly examine the ligand binding function of Cam GPIIb-IIIa, extracts of $^{125}$I surface-labeled platelets were subjected to affinity chromatography using an immobilized RGD peptide.

Platelets were isolated from acid-citrate dextrose anticoagulated human blood by differential centrifugation followed by gel filtration on Sepharose 2B (Ginsberg et al., *Blood*, 69:58 (1987)). Lysates of surface-labeled platelets were analyzed by KYGRGDS affinity chromatography as described by Lam et al., *J. Biol. Chem.*, 262:947 (1987). Briefly, intact platelets were radioiodinated by the lactoperoxidase-H$_2$O$_2$ method then resuspended to 2×10$^8$ platelets/mL and solubilized in lysis buffer containing 10 mmol/L N-2-hydroxyethylpiperazine-N'-2-ethanesulfonic acid (HEPES), pH 7.5, 0.15 mol/L NaCl, 1 mmol/L CaCl$_2$, 1 mmol/L MgCl$_2$, 0.1 mmol/L leupeptin, 1 mmol/L phenylmethanesulfonylfluoride (PMSF), 10 mmol/L N-ethylmaleimide, and 50 mmol/L octylglucoside. The lysates were incubated at 4° C. for 12 hours with KYGRGDS coupled to CNBr-activated Sepharose, washed, and eluted with 1 mmol/L GRGDSP. Under these conditions approximately 10% of normal GPIIb-IIIa is bound and eluted. A comparable quantity is bound on re-chromatography of the pass through fraction, indicating that less than 100% binding is due to the low affinity of the interaction rather than an inactive subpopulation of GPIIb-IIIa.

When surface-labeled normal platelets were passed over a KYGRGDS peptide matrix followed by the GRGDSP peptide, GPIIb and GPIIIa were bound and eluted. In contrast, with Cam platelets no such GPIIb-IIIa was eluted, even though the starting extract contained comparable quantities of surface-labeled GPIIb-IIIa. The GPIIb-IIIa content in the starting material and in the column fractions was quantitated by use of a polyclonal anti-GPIIb-IIIa antibody in an ELISA assay. The control extract contained 332 μg; the Cam individual contained 240 μg in the starting extract. The eluted fractions from the control extract contained 20 μg GPIIb-IIIa. In contrast, those from the Cam extract contained 2.6 μg. Thus, Cam GPIIb-IIIa has a deficit in the recognition of ligands such as RGD peptides.

5. Patients

The Cam variant of Glanzmann's thrombasthenia has been described in detail (Ginsberg et al., *J. Clin. Invest*, 78:1103 (1986)). Patients with this variant have near normal quantities of GPIIb-IIIa, undetectable fibrinogen binding to platelets, and absent platelet aggregation. The instant results were obtained on two affected male siblings with identical results.

A 58-year-old woman who noted increased bruising in 1984 was identified as having myeloproliferative disease (MPD). Studies showed a platelet count of 1,500,000/μL and a bone marrow with megakaryocytic hyperplasia and myelofibrosis. Since diagnosis, her bruising was constant, primarily involving her extremities and anterior chest, and she noted occasional epistaxis. She had four episodes of gastrointestinal bleeding, each requiring transfusion with 2 to 5 units (U) of RBCs. Before the onset of bruising, she had withstood several hemostatic challenges, including tonsillectomy, hemorrhoidectomy, and coccyxectomy, as well as three uncomplicated vaginal deliveries. A current physical examination was normal except for hepatosplenomegaly and generalized bruising. Recent laboratory findings: hematocrit 33, white blood cell count 29,600/μL with 27 neutrophils, 18 bands, 12 metamyelocytes, 11 myelocytes, 8 blasts, 2 monocytes, 21 lymphocytes, 7 basophils, and 6 nucleated RBCs. The patient had an abnormal bleeding time of >20 minutes and a normal coagulation profile (prothrombin time, activated partial thromboplastin time, thrombin time, and fibrin split products) and von Willebrand panel (von Willebrand antigen and ristocetin cofactor activity, and normal von Willebrand multimers distribution). Platelet aggregation studies, performed while receiving no medications, revealed absent aggregation to 10 and 100 μmol/L adenosine diphosphate (ADP), 50 μmol/L epinephrine, and collagen.

Reduced Platelet Aggregation in a Patient with Myelofibrosis is Caused by a Defect in the Activation of GPIIb-IIIa Next this strategy was applied to the characterization of a patient with myelofibrosis and an acquired severe defect in platelet aggregation. Platelets from this patient (MPD) did not express PAC1 binding sites when stimulated with 10 μm ADP (FIG. 3) or 50 μmol/L epinephrine (not shown), indicating a defect either in GPIIb-IIIa activation or ligand binding.

In contrast to the Cam patient, anti-LIBS1 and PMI-1 signals in the presence and absence of GRGDSP were similar to the normal control (FIG. 3), indicating intact ligand binding function. Furthermore, PAC1 bound to the MPD platelets in response to PMA, which circumvents normal receptor-mediated pathways by directly activating protein kinase C. The patient's platelets also exhibited normal α-granule secretion in response to PMA, as evidenced by surface expression of the α-granule protein thrombospondin. The aggregation defect in the patient's platelets could not be reversed by suspending her platelets in normal plasma, and the defect could not be induced in normal platelets by incubation in the patient's plasma. Thus, the GPIIb-IIIa from this patient has the potential to bind RGD ligands, but there appears to be an intrinsic cellular defect in receptor-mediated activation of GPIIb-IIIa.

6. Discussion of Examples 1-5

For two decades, studies of platelet aggregation in vitro have been routinely used in the characterization of patients with a prolonged bleeding time or a bleeding diathesis due to platelet dysfunction. The results of recent studies have demonstrated that normal aggregation requires the binding of fibrinogen to platelet GPIIb-IIIa. Furthermore, the aggregation process may be viewed as a series of necessary cellular events: (a) agonist-induced activation of GPIIb-IIIa, resulting in the exposure of the fibrinogen binding site; (b) fibrinogen binding; and (c) postoccupancy events that follow upon ligand binding (FIG. 1). Based on the flow cytometric approach described above, it is possible to classify disorders of platelet aggregation in terms of this series of events. The flow cytometry method used here is rapid and can be performed on platelet-rich plasma or on whole blood. This approach has been made possible by the availability of MoAbs that can distinguish between the resting, activated, and ligand-occupied forms of GPIIb-IIIa. The three types of platelet dysfunction that can lead to reduced platelet aggregation and the predicted flow cytometry results are summarized in Table 3.

TABLE 3

FLOW CYTOMETRIC ANALYSIS OF PLATELET AGGREGATION DYSFUNCTION

| Type of Defect | Response | | |
|---|---|---|---|
| | AGG[a] | PAC 1[b] | anti-LIBS 1[c] |
| None | + | + | + |
| Activation | − | − | + |
| Ligand Binding | − | − | − |
| Post-Occupancy | − | + or − | + or − |

Positive (+) or negligible (−) response.
[a]Agonist stimulated platelet aggregation.
[b]+ = Increased binding of activation dependent ligand (PAC 1 antibody) in response to agonist.
[c]+ = Increased binding of occupancy dependent antibody (anti-LIBS 1) in the presence of activation-independent ligand GRGDSP.

Using this approach, a variant of Glanzmann's thrombasthenia is found to be due to a defect in the ligand-binding function of GPIIb-IIIa and that the markedly reduced aggregation in a patient with myelofibrosis is due to a defect in agonist-specific activation of GPIIb-IIIa.

While a patient having postoccupancy dysfunction is not herein identified, patients having such a disorder may be subsequently identified. Postoccupancy defects may explain the process of agonist-induced platelet desensitization. For example, unstirred platelets activated for more than 10 minutes with ADP or epinephrine in the presence of fibrinogen demonstrate a marked reduction in their subsequent aggregation response when compared with the same platelets incubated without fibrinogen (Peerschke et al., Blood, 57:663 (1981); Shattil et al., Blood, 68:1224 (1986)). This can not be explained by a reduction in fibrinogen binding. Many patients are encountered in clinical practice with easy bruisability, a prolonged bleeding time, and a decreased platelet aggregation in response to one or more agonists. After excluding aspirin ingestion and storage pool disease, the underlying cause is usually inapparent. This group of individuals is often referred to as having "aspirinlike" defects, and some may have congenital or acquired platelet metabolic defects leading to an abnormality of GPIIb-IIIa activation. It seems likely that among this heterogeneous group of patients, individuals with the postoccupancy dysfunction phenotype will also be identified.

The Cam variant of thrombasthenia appears primarily due to a defect in ligand recognition by GPIIb-IIIa. This conclusion is based on (1) the failure of Cam GPIIb-IIIa to bind to an insolubilized RGD peptide and (2) a greater than 200-fold reduction in the capacity of activation-independent peptide ligands to increase the binding of the occupancy-dependent anti-LIBS1 antibody. Previous studies with proteolytic fragments of fibrinogen and fibrinogen-related peptides implicated recognition of RGD and fibrinogen gamma chain peptide sequences in fibrinogen binding (Kloczewiak et al., *Biochem. Biophys. Res. Commun.*, 107:181 (1982); Plow et al., *J. Biol. Chem.*, 59:5388 (1984); Plow et al., *Proc. Natl. Acad. Sci. USA*, 82:8057 (1985); Ginsberg et al., *J. Biol. Chem.*, 260:3931 (1985)). In the present study, GPIIb-IIIa lacking the capacity to bind these peptide sequences lacked the capacity to support fibrinogen binding and platelet aggregation. In view of the apparent autosomal-recessive inheritance of the Cam variant, the severe functional defect in GPIIb-IIIa, and the intermediate functional defect of the parents, it is likely that the basic Cam defect is due to a point mutation in GPIIb-IIIa (Ginsberg et al., *J. Clin. Invest.*, 78:1103 (1986)). Such a point mutation has recently been identified in a Cam patient (Loftus et al., *Blood*, 74:58A, suppl. 1 (1989)). The observation that this single amino acid change leads to loss of binding of both the RGD and gamma chain peptide sequences favors the possibility that both peptide sequences are recognized by a common binding site (Lam et al., *J. Biol. Chem.*, 263:12397 (1988)).

The PAC1 antibody was used to monitor GPIIb-IIIa activation because it binds selectively and with high affinity to stimulated platelets (Plow et al., *Proc. Natl. Acad. Sci. USA.* 82:8057 (1985)). Moreover, based on the inhibition of PAC1 binding by fibrinogen and fibrinogen-mimetic peptides and the capacity of peptides derived from the hypervariable region of PAC1 to inhibit fibrinogen binding, it seems likely that this antibody recognizes the ligand binding site in GPIIb-IIIa (Shattil et al., *Blood*, 73:150 (1989); Bennett et al., *J. Biol. Chem.*, 263:12948 (1988 ; Taub et al., *J. Biol. Chem.*, 264:259 (1989)). This hypothesis is strongly supported by the finding that PAC1 fails to recognize the Cam mutant GPIIb-IIIa, which lacks ligand binding function. The failure of PAC1 to interact with Cam platelets is unlikely to be due to gross denaturation of GPIIb-IIIa, because four other complex-specific anti-GPIIb-IIIa antibodies appeared to bind to the same extent as anti-GPIIb or anti-GPIIIa antibodies. Of these four antibodies, 7E3 binds more rapidly to activated cells and A₂A₉ is inhibited by synthetic peptides derived from the fibrinogen gamma chain (Coller et al., *J. Clin. Invest.*, 76:101 (1985)); Bennett et al., *J. Biol. Chem.*, 263:12948 (1988)). Because Cam GPIIb-IIIa lacks the capacity to recognize fibrinogen or the peptide ligands, it seems likely that these previous findings are due to an indirect relationship between the 7E3 and A₂A₉ epitopes and the ligand binding site of GPIIb-IIIa.

GPIIb-IIIa is a member of the Integrin family of structurally related adhesin receptors (Hynes et al., *Cell*, 48:549 (1987); Pytela et al., *Science*, 231:1559 (1986); Ginsberg et al., *J. Biol. Chem.*, 262:5437 (1987); Charo et al., *Proc. Natl. Acad. Sci. USA*, 83:8351 (1986)). Included in this family are a platelet collagen receptor, leukocyte receptors involved in inflammation and defense against pyogenic infection, and receptors involved in lymphocyte homing (Staatz et al., *J. Cell Biol.*, 108:1917 (1989); Anderson et al., *Annu. Rev. Med.*, 38:175 (1987); Holzmann et al., *Cell*, 56:37 (1989)). In the case of the leukocyte receptors, recent studies have reported that activation of these receptors induces leukocyte aggregation and endothelial cell adherence Harlan et al., *Blood*, 66:167 (1985)). Moreover, occupancy-dependent MoAbs have been prepared against an endothelial cell integrin (Frelinger et al., *J. Biol. Chem.*, 265:6346 (1990)). This suggests that activation-specific and occupancy-dependent antibodies can be prepared against other Integrins and can be used to analyze leukocyte dysfunction in a manner analogous to that described herein for GPIIb-IIIa. Indeed, these strategies should also allow rapid analysis of the binding functions of nonintegrin receptors as well.

7. Preparation of Anti-LIBS Antibodies

A. Isolation of GPIIb-IIIa (1) Platelet Isolation: Sixty milliliters (ml) of whole human blood was collected in 5 ml of ACD (0.065M citric acid, 0.085M sodium citrate, 2% dextrose) containing hirudin (Sigma Chemical Co., St. Louis, Mo.) at a final concentration of 0.06 units per milliliter (U/ml) and centrifuged for 15 minutes at 120×g. The resulting supernatant, designated platelet rich plasma (PRP), was recovered, isolated and further centrifuged for 15 minutes at 1200×g to form a pellet of isolated platelets. The supernatant formed is collected and used as platelet-poor plasma in other assays.

(2) GPIIb-IIIa Isolation from Platelets: A platelet pellet prepared as in Example 7A(1), was resuspended in 5 ml TBS (0.15M NaCl, 0.2M Tris, pH 7.4, 0.5 mM CaCl₂, 0.01 mM leupeptin) and sonicated on ice for 10 minutes at a maximum setting using a Model W-375 sonicator (Heat Systems Ultrasonics, Plainview, N.Y.). The sonicated suspension was twice frozen and thawed using a dry ice-methanol ice bath and stored at minus 20° C. The frozen-thawed platelet sonicate was layered on top of 5 ml of a sucrose solution (40% v/v in TBS), and centrifuged at 4C for one hour at 38,000 rotations per minute (RPM) in a SW41 centrifuge rotor (Beckman Instruments, Fullerton, Calif.) to form a milky colored infranatant. The milky-infranatant was then recovered and centrifuged at 43,000 RPM in a SW50.1 centrifuge rotor (Beckman) at 4C for one hour. The resulting pellet was resuspended in typically 1-2 ml TBS to form a platelet membrane solution, the protein concentration of which was determined to be in the range of 10–25 mg/ml, using the Bio-Rad Protein Assay Kit (Bio-Rad, Richmond, Calif.) according to the manufacturer's instructions.

The platelet membrane solution was again centrifuged in a SW50.1 centrifuge rotor as above and the resulting pellet was resuspended in 2 ml of extraction buffer (0.03M Tris, pH 7.4, 0.01 mM leupeptin, 200 mM n-octyl-beta-D-glucopyranoside; Calbiochem-Behring, La Jolla, Calif.). The platelet membrane extract thus formed was admixed thoroughly by vortexing and then maintained at room temperature for 30 minutes. The extract was thereafter centrifuged at 45,000 RPM in a SW50.1 centrifuge rotor for 1 hour at 4C and the platelet membrane extract supernatant thus formed was recovered.

The recovered supernatant was applied to a LKB Ultrogel Aca 34 gel filtration column 3×97 cm, LKB Instruments, Gaithersburg, Md.) that had been equilibrated with 1 liter of column buffer (0.03M Tris, pH 7.4, 0.1 mM CaCl₂, 0.1% n-octyl-beta-D-glucopyranoside) and 5 ml fractions were collected from the resulting column effluent. The optical density at 280 nanometers of each fraction was determined and fractions around the several peaks were combined to form a pool for each peak. Samples from each pool were analyzed by electrophoresis in 6% polyacrylamide slab gels using the reducing buffers and procedures described by Laemmli, *Nature (London)*, 227:680–685 (1970), and low molecular weight protein standards ranging in size from 14.4 kilodaltons (KDa) to 92.5 KDa (Bio-Rad, Richmond, Calif.). The pool containing predominantly two protein species having molecular weights corresponding to GPIIb and GPIIIa, i.e., 120 KDa and 100 KDa, respectively was recovered. The protein concentration of the isolated GPIIb-IIIa preparation thus prepared was typically determined using the Bio-Rad Protein Assay Kits to be in the range of 0.3 to 0.8 mg/ml.

(3) Polypeptide Affinity Isolation of GPIIb-IIIa: Synthesis of peptide of the formula Gly-Arg-Gly-Asp-Ser-Pro-Lys was accomplished using the technique of Merrifield, *J. Am. Chem. Soc.*, 85:2149-54 (1963) or purchased from Peninsula Laboratories (Belmont, Calif.). All peptides were greater than 90% homogenous when analyzed by high performance liquid chromatography (HPLC) utilizing a $C_{18}$ bondapak column and a 0-60% linear gradient of acetonitrile in 0.1% trifluoroacetic acid. Affinity matrices containing the immobilized peptide Gly-Arg-Gly-Asp-Ser-Pro-Lys were prepared by coupling the peptide to cyanogen bromide-activated Sepharose 4B (Pharmacia P-L Biochemicals, Piscataway, N.J.) according to the manufacturer's instructions. The affinity matrix containing the immobilized peptide was packed into columns (0.7×15 cm) and equilibrated with PBS at pH 7.5 containing 50 mM octylglucoside, 1 mM phenylmethanesulfonylfluoride (PMSF), 1 mM $CaCl_2$ and 1 mM $MgCl_2$ at 4C. The platelet membrane extract supernatant prepared according to Example 7A(2) was applied to the affinity matrix containing Gly-Arg-Gly-Asp-Ser-Pro-Lys. The unbound proteins were eluted with 100 ml of PBS at pH 7.5, containing 25 mM octylglucoside, 1 mM PMSF, 1 mM $CaCl_2$, and 1 mM $MgCl_2$ (column buffer). Bound GPIIb-IIIa was then eluted by washing the column with 10 ml of column buffer containing the designated peptide at a concentration of 1.7 mM followed by another 10 ml of column buffer. Fractions of 2.5 ml each were collected, and the proteins in each fraction were analyzed by electrophoresis on sodium dodecyl sulfate-polyacrylamide gels (7.5%) after reduction with 10% 2-mercaptoethanol. The protein bands were visualized by staining with Coomassie Blue according to the methods described in *Current Protocols in Molecular Biology*, Ausubel et al., eds., John Wiley and Sons, N.Y., 1987.

(4) Immunoaffinity Isolation of GPIIb-IIIa: An immunoaffinity column was prepared by coupling the antibody PMI-1 (which binds to GPIIb, ATCC, Rockville, Md.) to Affi-Gel 10 (Biorad, Richmond, Calif.) at 4 mg of antibody per ml of resin using the instructions provided by the manufacturer of the activated resin. Platelets prepared according to Example 1A ($6 \times 10^{10}$) were lysed in 1 ml of 50 mM octylglucoside in a column buffer consisting of 10 mM N-[2-hydroxyethyl] piperazine-N-[2'ethanesulfonic acid] (HEPES), 1 mM $CaCl_2$, 1 mM $MgCl_2$, 0.15M NaCl, 1 mg/ml phenylmethane sulfonylfluoride (PMSF), 1.25 mg/ml N-ethyl-maleimide and 0.1 mg/ml leupeptin. The insoluble material was removed by centrifugation at 45,000 RPM in an SW 50.1 rotor for one hour at 4C. The supernatant, designated as platelet lysate, was collected, the peptide Gly-Arg-Gly-Asp-Ser-Pro (GRGDSP) was admixed at 1 mM, and thereafter admixed with 2 ml of antibody-Affi-Gel 10 and maintained for 12 to 18 hours at 4C. This admixture was then placed into a column and washed with 10 column volumes of column buffer containing 1 mM of the peptide Gly-Arg-Gly-Asp-Ser-Pro and 25 mM octylglucoside, and eluted with five column volumes of column buffer at pH 5 containing 25 mM octylglucoside and no peptide. The eluted fractions were immediately neutralized to pH 7.2, pooled and dialyzed against column buffer containing 5 mM octylglucoside. The protein concentration of the isolated GPIIb-IIIa preparation thus prepared was determined using the Bio-Rad Protein Assay Kit.

B. Preparation of Monoclonal Antibody Compositions

Monoclonal antibodies that activate GPIIb-IIIa and immunoreact with a ligand-induced binding site on GPIIb-IIIa were produced using standard hybridoma technology with exceptions as noted. Briefly, two Balb/c mice were each immunized intraperitoneally four times at one week intervals with increasing doses (1 ug, 10 ug, 25 ug, 50 ug and 100 ug, respectively) of immunogen consisting of the receptor-ligand complex comprised of affinity-isolated GPIIb-IIIa, as prepared in Example 7A(3) (1.25 mg/ml) and peptide Gly-Arg-Gly-Asp-Ser-Pro at 3 mg/ml. The immunogen was diluted 1:1 in Complete Freund's Adjuvant for the first immunization, in Incomplete Freund's Adjuvant for the second and third immunization, and in normal saline for the fourth. Three days after the fourth immunization about $1 \times 10^8$ lymphocytes were isolated from the spleens of both mice, admixed into a suspension and fused with $5 \times 10^7$ P3X63AG8.053 mouse myeloma cells using 50% PEG 1500 as the cell fusion promoter. The resulting transformed (fused) antibody-producing cells (hybridomas) were initially transferred to 96-well microtiter plates at a density of about $1 \times 10^6$ cells per well and cultured in selective HAT media.

Tissue culture supernatants from about 2000 wells appearing to contain viable HAT resistant hybridoma cells after 8 days of culturing were screened in the ELISA assay described in Example 7C(1) for the presence of antibody molecules that immunoreact with plastic-immobilized GPIIb-IIIa. About 44 hybridoma cultures were identified that produced GPIIb-IIIa-immunoreacting antibody molecules. The isolated hybridomas were then subcloned twice at limiting dilutions to provide about 1 cell per well. Twenty four of the resulting hybridoma cultures were shown to be of monoclonal origin on the basis of three criteria: (1) each supernatant was from a single cell foci and immunoreacted with GPIIb-IIIa in the ELISA screen, (2) each supernatant showed a single homogeneous band when analyzed by cellulose acetate gel electrophoresis according to the method described in *Monoclonal Antibodies: Principles and Practice*, J. W. Goding, ed., Academic Press, Inc., Orlando, Fla., 1983, and (3) each supernatant contained a single isotype of immunoglobulin when analyzed using the Mouse Ig Screening and Isotyping Kit according to the instructions provided by the manufacturer, Boehringer-Mannheim Biochemicals, Indianapolis, Ind. Results of the isotype analysis of some of the hybridoma supernatants characterized are shown in Table 4.

TABLE 4

| | GRGDSP Modulation Of LIBS Epitope Expression In ELISAs To Identify Anti-LIBS Monoclonal Antibody | | | | |
|---|---|---|---|---|---|
| | Subunit[a] | | $B/B_0$[b] | | % |
| Mab | Specificity | Isotype | − | + | Decrease[c] |
| LIBSa | GPIIIa | $G_1K$ | 0.61 | 0.32 | 48 |
| LIBSb | GPIIIa | $G_{2a}K$ | 0.62 | 0.35 | 44 |
| LIBSc | GPIIIa | $G_1K$ | 0.45 | 0.21 | 53 |
| LIBSd | GPIIIa | $G_{2b}K$ | 0.79 | 0.62 | 22 |
| LIBSe | GPIIIa | $G_1K$ | 0.82 | 0.52 | 37 |
| LIBSf | GPIIIa | ND[d] | 0.29 | 0.17 | 41 |

TABLE 4-continued

GRGDSP Modulation Of LIBS Epitope Expression
In ELISAs To Identify Anti-LIBS Monoclonal Antibody

| Mab | Subunit[a] Specificity | Isotype | B/B₀[b] − | B/B₀[b] + | % Decrease[c] |
|---|---|---|---|---|---|
| LIBSg | GPIIIa | ND | 0.64 | 0.51 | 20 |
| LIBSh | GPIIIa | G$_{2a}$K | 0.38 | 0.28 | 26 |
| LIBSi | GPIIIa | G$_{2a}$K | 0.22 | 0.17 | 23 |
| PMI-2[e] | GPIIIa | G$_{2a}$K | 0.58 | 0.46 | 21 |
| Mab15 | GPIIIa | G$_1$K | 0.25 | 0.23 | 8 |
| Mab19 | GPIIIa | MK | 0.32 | 0.32 | 0 |
| Mab23 | GPIIIa | G$_{2a}$K | 0.17 | 0.15 | 12 |
| LIBSj | hGPIIb | MK | 0.90 | 0.70 | 22 |
| PMI-1[e] | hGPIIb | G$_{2b}$K | 0.98 | 0.36 | 63 |
| Mab13 | hGPIIb | G1K | 0.61 | 0.51 | 16 |
| Mab10 | hGPIIb | G$_1$K | 0.84 | 0.79 | 6 |
| Mab18 | lGPIIb | MK | 0.40 | 0.34 | 15 |
| Mab16 | lGPIIb | MK | 0.54 | 0.47 | 13 |
| Mab5 | lGPIIb | MK | 0.66 | 0.64 | 3 |
| LIBSk | | G$_1$K | 0.80 | 0.59 | 26 |
| Mab38 | | G$_1$K | 0.82 | 0.69 | 16 |
| Mab51 | | ND | 0.76 | 0.73 | 4 |

[a]Subunit specificity was determined by Western blotting as described in Example 7B.
[b]B/B₀ indicates the ratio of the measured absorbance at A490 in the presence (B) of platelet lysate (equivalent to 5 × 10⁸ platelets/ml) to the measured absorbance at A490 in the absence (B₀) of lysate. The ratio B/B₀ was determined both in the presence (+) of GRGDSP (1 mM) and in the absence (−) of GRGDSP.
[c]A change in B/B₀ upon addition of GRGDSP indicates the presence of a LIBS. Antibodies were considered to be anti-LIBS if the percent change in B/B₀ was greater than 20%.
[d]ND = Not determined.
[e]PMI-1 and PMI-2 were generated in a separate immunization and fusion using platelet membranes as the immunogen as described by Shadle et al., J. Cell Biol., 99:2056–60 (1984), and were screened for anti-LIBS activity as described herein.

The above screening procedure resulted in the identification of 22 hybridomas that produce antibody molecules that immunoreact with plastic-immobilized GPIIb-IIIa.

To identify hybridomas that produce antibody molecules that immunoreact with a ligand-induced binding site (LIBS) on GPIIb-IIIa (i.e., a GPIIb-IIIa LIBS), a competition ELISA screen was conducted as described in Example 7C(2) discussed hereinafter, in which the immunoreaction admixture was maintained in the presence and absence of a GPIIb-IIIa specific ligand to express a GPIIb-IIIa LIBS. Anti-GPIIb-IIIa LIBS antibody molecules are those that exhibit a greater affinity of immunoreaction with GPIIb-IIIa when measured in the presence of a GPIIb-IIIa specific ligand as compared to the measurement in the absence of specific ligand, such that the greater affinity represents a change in the ratio of the absorbance at 490 nm (B/B₀) of greater than 20% when measured in the presence (as compared to the absence) of GPIIb-IIIa specific ligand.

Twelve hybridomas were identified from the group of twenty two hybridomas in Table 4 that produce antibody molecules that immunoreact with GPIIb-IIIa LIBS, and the hybridomas are designated herein as LIBSa-LIBSm, as shown in Table 4.

In addition, it is seen that other anti-LIBS antibody molecules have been isolated by the disclosed methods, as shown in Table 4, that immunoreact with other LIBS epitopes present on the GPIIb or GPIIIa subunits of the platelet receptor.

Particularly preferred are the antibodies that exhibit enhanced affinity for immunoreaction with a LIBS epitope as detected in Table 4. These are antibodies that exhibit greater than 25 percent, preferably 30 percent, and more preferably 40 percent, change in B/B₀ upon addition of the specific ligand.

The locations of the particular GPIIb-IIIa LIBS detected by the monoclonal antibodies shown in Table 4 were mapped to subunit regions of the platelet receptor by western immunoblotting according to the general methods described by Towbin et al., Proc. Natl. Acad. Sci U.S.A., 76:4350–54, (1979). Briefly, GPIIb-IIIa isolated in Example 7A(2) was subjected to electrophoresis on 7.5% SDS polyacrylamide gels (SDS-PAGE) under reducing conditions, transferred to a membrane and immunoreacted with supernatants of the hybridomas shown in Table 4. The immunoreaction products formed between the monoclonal antibodies provided in the hybridoma supernatants and the GPIIb-IIIa protein subunits on the membranes were detected using biotinylated second antibody and avidin-conjugated peroxidase according to manufacturer's instructions (Vectastain ABC Method, Vector Laboratories, Burlingame, Calif.).

The results of the Western immunoblot mapping showed that most of the hybridoma supernatants contained antibody molecules that immunoreacted with a protein having an apparent molecular weight on SDS-PAGE of 120 kilodaltons (KDa), 20 KDa or 100 KDa, corresponding to GPIIb heavy chain (hGPIIb), GPIIb light chain (lGPIIb) or GPIIIa, respectively. In a few cases, the antibody molecules did not react with any of the isolated GPIIb-IIIa subunits, leaving their subunit specificity uncharacterized. The determined subunit specificities are shown in Table 4.

Thus it is seen that the monoclonal antibody molecule produced by hybridoma LIBSa for example, which antibody molecule is also referred to herein as LIBSa and as LIBS1, immunoreacts with the GPIIIa subunit of the GPIIb-IIIa platelet receptor. In addition the LIBSa antibody molecule immunoreacts with the LIBS1 epitope present on a receptor-ligand complex comprised of GPIIb-IIIa and a GPIIb-IIIa specific ligand.

Monoclonal antibody compositions comprised of isolated antibody molecules were also prepared by isolating the antibody molecules from the ascites fluid of a mouse containing one of the hybridoma cell lines shown in Table 4 using protein A-Sepharose typically obtained from Pharmacia Inc. (Piscataway, N.J.) and used according to manufacturer's instructions.

The protein concentration of isolated antibody molecule compositions as needed was determined using the Bio-Rad Protein Assay Kit (Bio-Rad, Richmond, Calif.) according to the manufacturer's instructions.

To prepare a monoclonal antibody composition containing $^{125}$I-labeled antibody molecules, 350 microliters (ul) of PBS (0.15M NaCl, 0.01M sodium phosphate, pH 7.09) containing 1 milligram per milliliter (mg/ml) of the above isolated antibody molecules were admixed with 40 micrograms (ug) of chloramine-T and 1 milliCurie (mCi) of carrier-free Na$^{125}$I (Amersham, Arlington Heights, Ill.). The resulting admixture was maintained for 5 minutes at about 20° C. and then admixed with 20 ul of a 2 mg/ml sodium metabisulfite solution (2 mg/ml) and 20 ul of a potassium iodide solution. Thereafter, 800 ul of PBS containing 1% BSA were admixed followed by further admixture of disopropylfluorophosphate to a final concentration of 10 mM. The resulting admixture was maintained for 60 minutes at 22° C. and then dialyzed against PBS. The specific activity of the resulting $^{125}$I-labeled antibody molecules was about 4.5 microCurie (uCi) per ug.

Compositions containing Fab fragments from the above isolated antibody molecules were prepared by digestion with papain (200:1 weight per weight of Ig to papain) for 6 hours at 37° C. following the methods of Mage et al., *Methods in Enzymology*, 70:142–150 (1980). Undigested Ig and Fc fragments were removed by chromatography on protein A-Sepharose. The resulting Fab fragments-containing compositions were then ready for use, or were $^{125}$I-labeled, as needed, using the same procedures as described above for monoclonal antibody compositions.

C. ELISA Assays (1) ELISA To Screen Monoclonal Antibodies: Antibody molecules contained in hybridoma culture supernatants were examined for their ability to immunoreact with GPIIb-IIIa immobilized on plastic. Fifty microliters (ul) of coating solution (0.1M NaHCO$_3$, pH 8.0, 0.1% NaN$_3$) containing 10 ug/ml of isolated GPIIb-IIIa prepared in Example 7A(1) were admixed into the wells of flat-bottom 96-well microtiter plates (Immulon 2; Dynatech Laboratories, Chantilly, Va.). The plates were then maintained for 60 minutes at 37° C. to permit the GPIIb-IIIa to adsorb onto the walls of the wells. The coating solution was removed by shaking, the wells were rinsed twice with washing buffer (10 mM Tris at pH 7.4, 0.05% (v/v) TWEEN-20, 0.15M NaCl, and 200 mg/ml merthiolate), and 200 ul of blocking solution [5% bovine serum albumin (BSA;w/v) in coating solution] were admixed into each well (solid support) to block excess protein sites.

The wells were maintained for 60 minutes at about 37° C. and then the blocking solution was removed. About 50 ul of hybridoma culture supernatant diluted 1:1 in dilution buffer consisting of 0.1% (w/v) BSA in washing buffer was added to each well to form an immunoreaction admixture. The resulting solid/liquid phase immunoreaction admixtures were maintained at room temperature for 60 minutes to permit formation of a first solid phase-bound immunoreaction product between the solid phase-bound GPIIb-IIIa-ligand complex and admixed antibodies. The solid and liquid phases were then separated, the wells were rinsed twice with washing buffer, and excess liquid was removed by shaking.

Fifty ul of a solution containing horseradish peroxidase labeled goat anti-mouse IgG (Tago Inc., Burlingame, Calif.), diluted 1:1000 in dilution buffer was admixed into each well to form a second solid/liquid phase immunoreaction admixture (labeling immunoreaction admixture). The wells were maintained for 60 minutes at room temperature to permit formation of a second immunoreaction product between the labeled antibody and any solid phase-bound antibody of the first immunoreaction product and then rinsed twice with washing buffer to isolate the solid phase-bound label-containing immunoreaction products. Excess liquid was then removed from the wells.

Fifty ul of freshly prepared chromogenic substrate solution containing 4.0 mg/ml 0-phenylenediamine and 0.012% (v/v) hydrogen peroxide in CP buffer (243 ml of 0.1M citric acid and 250 ml of 0.2M dibasic sodium phosphate per liter H$_2$O, pH 5.0) o were then admixed into each well to form a color developing-reaction admixture. After maintaining the color developing-reaction admixture for 10 minutes at about 20° C., 50 ul of 2N H$_2$SO$_4$ were admixed into each well to stop the developing-reaction, and the resulting solutions were assayed for absorbance at 490 nanometers (nm) light wavelength using a Model 310 ELISA plate reader (Bio-Tek Instruments, Winooski, Vt.).

Antibody molecule compositions were considered to contain anti-GPIIb-IIIa immunoreactive antibody molecules if the measured absorbance at 490 nm (A490) was at least 6 times above background i.e., above about 0.3 optical density units when measured at A490.

(2) Competition ELISA To Detect Anti-LIBS Antibodies:

Antibody molecules contained in antibody compositions were examined for their ability to immunoreact with GPIIb-IIIa LIBS in a competition ELISA conducted similarly to the ELISA described in Example 7C(1) with the following exceptions as noted.

Before an antibody composition was added to a GPIIb-IIIa coated microtiter wells, 20 ul of ELISA assay buffer consisting of 10 mM TRIS-HCl at pH 7.4, 0.15M NaCl, 0.05% (v/v) TWEEN-20, 0.02% (w/v) sodium merthiolate, 5 mM CaCl$_2$, 5 mM MgCl2 and 0.1% (w/v) BSA was added to each microtiter well. Then 10 ul of a solution containing platelet lysate at $2 \times 10^7$ platelets per ml, prepared as in Example 7A(4), was added to one set of wells and platelet lysate was omitted from a second set of wells. To both sets, with or without platelet lysate, was added 10 ul of a second solution that contained either 0 or 5 mM of the RGD-containing polypeptide ligand GRGDSP in ELISA assay buffer. Thereafter, 10 ul of an antibody composition at 0.3 μg/ml was added to both sets of wells at an antibody concentration diluted in ELISA assay buffer so as to be the limiting component in the ELISA immunoreaction admixture. Antibody concentrations are present as a limiting component when it has been diluted in ELISA assay buffer to produce an optical density at A490 of about 1.0 when measured using the ELISA assay of Example 7C(1) with the exception that ELISA assay buffer is used in place of dilution buffer.

The results obtained in each immunoreaction admixture were measured for the presence of a developed color reaction as before. Absorbance measured in wells that contained no platelet lysate is referred to as B$_0$, and the absorbance measured in wells that contained platelet lysate is referred to as B. A ratio of absorbance is calculated for B/B$_0$, and expressed as measured either in the presence (+) or absence (−) of RGD-containing ligand (GRGDSP). The expression of a LIBS cryptic antigenic determinant is determined by calculating the percentage decrease observed in B/B$_0$ when ligand is added to the GPIIb-IIIa contained in platelet lysate in the immunoreaction admixture. A decrease upon addition of ligand in B/B$_0$ that exceeds 20% indicates an antibody molecule that immunoreacts with a LIBS epitope. Table 4 shows the results of Competition ELISA for monoclonal antibody molecules prepared in Example 7B that immunoreact with GPIIb-IIIa.

8. Fibrinogen Binding to Activated Platelets

Fibrinogen was isolated and labelled with $^{125}$I by standard methods as described by Marguerie et al., *J. Biol. Chem.*, 255:154–161 (1980) to form $^{125}$I-Fg. Thereafter, the binding of $^{125}$I-Fg to platelets was assayed as described previously. Marguerie et al., *J. Biol. Chem.*, 255:154–161 (1980). Binding was initiated by the admixture of a million resting platelets in the presence or absence of 10 micromolar adenosine diphosphate (ADP) to radiolabelled fibrinogen at varying concentrations from 0.01 to 1 nanomolar (nM) and incubation at 37 degrees for 30 minutes. Bound fibrinogen was separated from free fibrinogen by centrifugation of the platelet-fibrinogen admixture through 0.3 ml of 20% sucrose and the amount of radiolabelled fibrinogen associated with the cell pellet determined by gamma detection.

Addition of 10 uM ADP to the platelets was observed to stimulate at least a three fold increase in the number of $^{125}$I-Fg molecules that bound the platelets. Unstimulated platelets exhibited no increase in binding to $^{125}$I-Fg above background. Therefore, activation of platelets is detected where the amount of bound fibrinogen is at least three-fold greater than the amount bound when platelets are not stimulated by ADP.

Although the present invention has been described in some detail by way of illustration and example for purposes of clarity and understanding, it will be obvious that certain modifications may be practiced within the scope of the appended claims.

What is claimed is:

1. A method for characterizing a platelet adhesion defect in a patient having said defect as an activation, ligand binding, or post-occupancy defect, said method comprising:
    (a) determining the presence of activation competent platelets in a first platelet-containing sample from said patient;
    (b) determining the presence of ligand-occupancy competent platelets in a second platelet-containing sample from said patient; and
    (c) correlating the results in steps (a) and (b) with predetermined criteria for characterizing platelet adhesion defects, whereby (i) activation defects are identified when the presence of activation competent platelets is less than a predetermined activation level using said predetermined criteria, (ii) ligand binding defects are identified when the presence of ligand-occupancy competent platelets is less than a predetermined ligand-occupancy level using said predetermined criteria, and (iii) post-occupancy defects are identified when the presence of activation competent platelets exceeds said predetermined activation level and the presence of ligand-occupancy competent platelets exceeds said predetermined ligand-occupancy level.

2. The method of claim 1 wherein steps (a) and (b) employ fluorescence activated flow cytometry to determine the presence of activation competent and ligand-occupancy competent platelets.

3. The method of claim 1 wherein step (a) comprises:
    (i) admixing said first sample with a predetermined amount of a platelet agonist sufficient to activate normal platelets, and with an activation specific ligand (ASL) that preferentially binds activated platelets, to form a reaction admixture;
    (ii) maintaining said reaction admixture under predetermined biological assay conditions for a time period sufficient for activated normal platelets to form a reaction product with said ASL; and
    (iii) determining the amount of reaction product formed in step (ii), thereby determining the presence of activation competent platelets in said sample.

4. The method of claim 3 wherein said activation specific ligand is a monoclonal antibody.

5. The method of claim 3 wherein said activation specific ligand is fibrinogen.

6. The method of claim 1 wherein step (b) comprises:
    (i) admixing said second sample with a predetermined amount of an activation independent ligand (AIL) that forms a ligand-induced binding site (LIBS) on normal platelets, and with an anti-LIBS antibody that preferentially binds to said LIBS to form an immunoreaction admixture;
    (ii) maintaining said immunoreaction admixture under predefined biological assay conditions for a time period sufficient for the anti-LIBS antibody to immunoreact with said LIBS to form an immunoreaction product; and
    (iii) determining the amount of immunoreaction product formed in step (ii), thereby determining the presence of ligand-occupancy competent platelets in said sample.

7. The method of claim 6 wherein said anti-LIBS antibody is a monoclonal antibody.

8. The method of claim 7 wherein said monoclonal antibody is the antibody produced by hybridoma PMI-1, having ATCC accession number HB 9476.

9. The method of claim 6 wherein the activation independent ligand is selected from the group consisting of RGD, LGGAKQAGDV, KYGRGDS, GRGDSP, and KQAGDV.

10. The method of claim 1 wherein step (b) comprises:
    (i) admixing said second sample with a predetermined amount of a platelet agonist sufficient to activate normal platelets, and with an activation specific ligand (ASL) that preferentially binds activated platelets to form a ligand-induced binding site (LIBS), and with an anti-LIBS antibody, which preferentially binds to said LIBS, to form a reaction admixture thereof;
    (ii) maintaining said reaction admixture under predefined biological assay conditions for a time period sufficient for the anti-LIBS antibody to immunoreact with said LIBS to form an immunoreaction product; and
    (iii) determining the amount of immunoreaction product formed in step (ii), thereby determining the presence of ligand-occupancy competent platelets in said sample.

11. The method of claim 10, wherein said activation specific ligand is fibrinogen.

12. The method of claim 10 wherein said anti-LIBS antibody is a monoclonal antibody.

13. The method of claim 12 wherein said monoclonal antibody is the antibody produced by hybridoma PMI-1, having ATCC accession number HB 9476.

* * * * *